United States Patent
Tada et al.

(10) Patent No.: US 11,270,433 B2
(45) Date of Patent: Mar. 8, 2022

(54) DISEASE DIAGNOSIS SUPPORT METHOD EMPLOYING ENDOSCOPIC IMAGES OF A DIGESTIVE ORGAN, A DIAGNOSIS SUPPORT SYSTEM, A DIAGNOSIS SUPPORT PROGRAM AND A COMPUTER-READABLE RECORDING MEDIUM HAVING THE DIAGNOSIS SUPPORT PROGRAM STORED THEREIN

(71) Applicant: AI MEDICAL SERVICE INC., Tokyo (JP)

(72) Inventors: Tomohiro Tada, Saitama (JP); Kazuharu Aoyama, Saitama (JP); Hirotoshi Takiyama, Saitama (JP); Tsuyoshi Ozawa, Saitama (JP); Yuma Endo, Saitama (JP); Youichi Kumagai, Saitama (JP)

(73) Assignee: AI MEDICAL SERVICE INC., Tokyo (JP)

( * ) Notice: Subject to any disclaimer, the term of this patent is extended or adjusted under 35 U.S.C. 154(b) by 122 days.

(21) Appl. No.: 16/620,861

(22) PCT Filed: May 11, 2018

(86) PCT No.: PCT/JP2018/018316
§ 371 (c)(1),
(2) Date: Dec. 9, 2019

(87) PCT Pub. No.: WO2018/225448
PCT Pub. Date: Dec. 13, 2018

(65) Prior Publication Data
US 2020/0279368 A1 Sep. 3, 2020

(30) Foreign Application Priority Data

Jun. 9, 2017 (JP) .............................. JP2017-114792
Nov. 2, 2017 (JP) .............................. JP2017-213311

(51) Int. Cl.
G06K 9/00 (2006.01)
G06T 7/00 (2017.01)
(Continued)

(52) U.S. Cl.
CPC ........ G06T 7/0012 (2013.01); A61B 1/00016 (2013.01); G06T 7/11 (2017.01);
(Continued)

(58) Field of Classification Search
CPC ......... G06T 7/0012; G06T 7/143; G06T 7/11; G06T 2207/10068; G06T 2207/20076;
(Continued)

(56) References Cited

U.S. PATENT DOCUMENTS

2008/0260226 A1 10/2008 Moriya
2018/0225820 A1* 8/2018 Liang .................... G06K 9/627
(Continued)

FOREIGN PATENT DOCUMENTS

CN 104732243 A 6/2015
CN 205665697 U 10/2016
(Continued)

OTHER PUBLICATIONS

C. Huang, P. Chung, B. Sheu, H. Kuo and M. Popper, "Helicobacter Pylori-Related Gastric Histology Classification Using Support-Vector-Machine-Based Feature Selection," in IEEE Transactions on Information Technology in Biomedicine, vol. 12, No. 4, pp. 523-531, Jul. 2008, doi: 10.1109/TITB.2007.913128. (Year: 2008).*
(Continued)

*Primary Examiner* — Atiba O Fitzpatrick
(74) *Attorney, Agent, or Firm* — Hauptman Ham, LLP

(57) ABSTRACT

Provided is a disease diagnosis support method employing endoscopic images of a digestive organ using a neural network, and the like. The disease diagnosis support method employing endoscopic images of a digestive organ using a
(Continued)

neural network trains the neural network by using first endoscopic images of the digestive organ, and corresponding to the first endoscopic images, at least one of definitive diagnosis result of being positive or negative for the disease of the digestive organ, a past disease, a severity level, and information corresponding to an imaged region. The trained neural network outputs, based on second endoscopic images of the digestive organ, at least one of a probability of being positive and/or negative for the disease of the digestive organ, a probability of a past disease, a severity level of the disease, and the information corresponding to the imaged region.

32 Claims, 15 Drawing Sheets

(51) Int. Cl.
  *G06T 7/143* (2017.01)
  *G06T 7/11* (2017.01)
  *A61B 1/00* (2006.01)
(52) U.S. Cl.
  CPC .... *G06T 7/143* (2017.01); *G06T 2207/10068* (2013.01); *G06T 2207/20076* (2013.01); *G06T 2207/20081* (2013.01); *G06T 2207/20084* (2013.01); *G06T 2207/30032* (2013.01); *G06T 2207/30092* (2013.01); *G06T 2207/30096* (2013.01)
(58) Field of Classification Search
  CPC . G06T 2207/20081; G06T 2207/20084; G06T 2207/30032; G06T 2207/30092; G06T 2207/30096; A61B 1/00016
  See application file for complete search history.

(56) References Cited

U.S. PATENT DOCUMENTS

| | | | | |
|---|---|---|---|---|
| 2018/0247153 | A1* | 8/2018 | Ganapati | A61B 1/005 |
| 2018/0253839 | A1* | 9/2018 | Zur | G06T 7/0012 |
| 2019/0034800 | A1* | 1/2019 | Shiratani | G06N 3/0427 |
| 2019/0311476 | A1* | 10/2019 | Hayami | G06T 7/70 |

FOREIGN PATENT DOCUMENTS

| | | |
|---|---|---|
| CN | 106372390 A | 2/2017 |
| JP | 2002165757 A | 6/2002 |
| JP | 200995644 A | 5/2009 |
| JP | 2013113689 A | 6/2013 |
| JP | 201745341 A | 3/2017 |
| JP | 201767489 A | 4/2017 |
| WO | 2016094330 A2 | 6/2016 |
| WO | 2017055412 A1 | 4/2017 |

OTHER PUBLICATIONS

Yoichi Mori et al, "Novel computer-aided diagnostic system for colorectal lesions by using endocytoscopy (with videos)", Gastrointestinal Endoscopy, 2015, p. 621-p. 629, vol. 81, No. 3, Chicago, USA, www.giejournal.org, 9pp.
"Learning skin lesion: Artificial intelligence reinforces ability to detect skin cancer based on images", Nature;opening article, Feb. 2017, www.natureasia.com/en/US/nature/highlights/82762, 7pp.
"About the new endoscopy system (NBI)",http://gentaikyo.or.jp/about/pdf/report/131119.pdf, 4pp.
Kumagai Y et al., "Magnifying Chromoendoscopy of the Esophagus: In-Vivo Pathological Diagnosis Using an Endocytoscopy System", Endoscopy, 2004, vol. 36(7), p. 590-594, New York, 5pp.
Esteva A, et al. "Dermatologist-level classification of skin cancer with deep neural networks", Nature, Feb. 2, 2017, vol. 542, p. 115-126, Macmillan Publishers Limited, 12pp.
Inui M. et al., "Methods for examining gastric cancer", Biken Journal vol. 37, No. 3, 2014, 10pp.
Sekino et al., "Improvement of Convolutional Neural Network Character Recognition Based on Visual Information Processing Model", The 27th Annual Conference of the Japanese Society for Artificial Intelligence, 1pp-4pp, 2013, 4pp.
Sekino et al., "Improved Convolutional Neural Network Character Recognition Based on Visual Information Processing Model", Fuji Xerox technical report No. 23, 82pp-88pp, 2014, 7pp.
Office Action in SG application No. 11201911791R, dated Jun. 28, 2021, 6pp.
Office Action in TW application No. 107116169, dated Aug. 3, 2021, 34pp.
Office Action in CN application No. 201880037797.9, dated Dec. 30, 2021, 41pp.

* cited by examiner

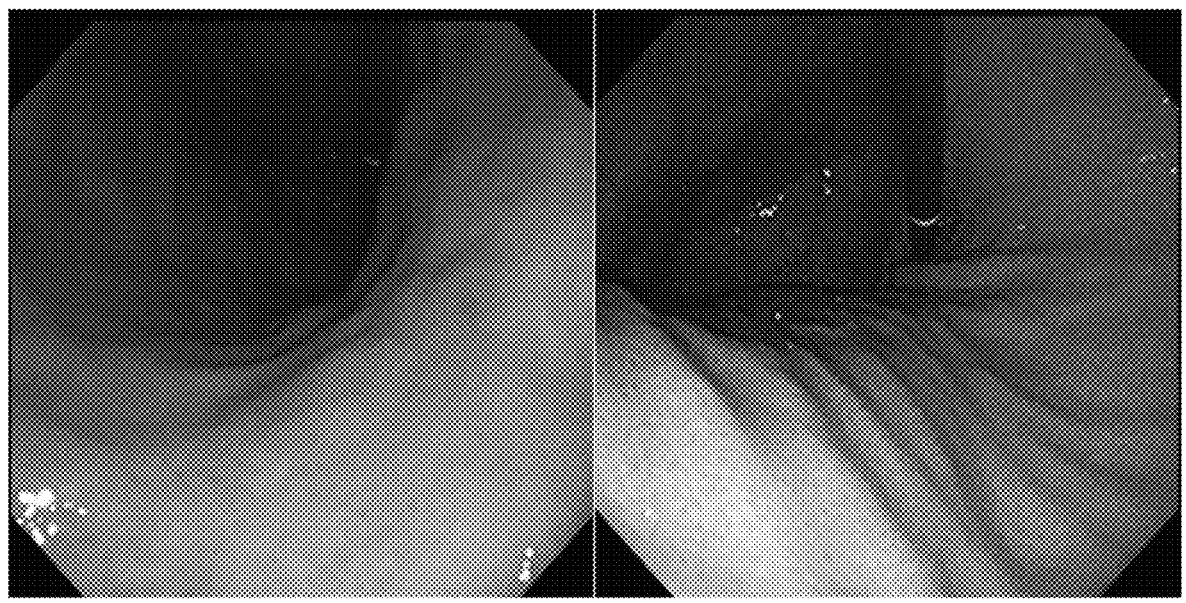
FIG.1A  FIG.1B
FIG. 2
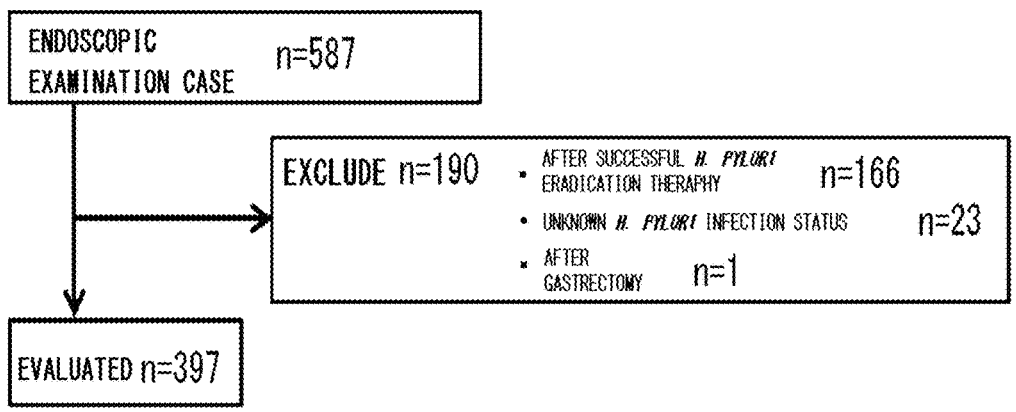

FIG. 18
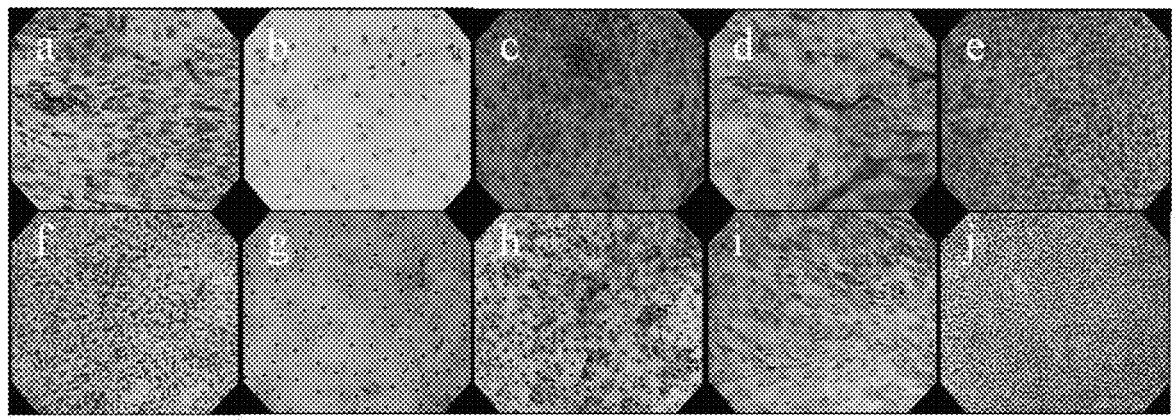
FIG. 19
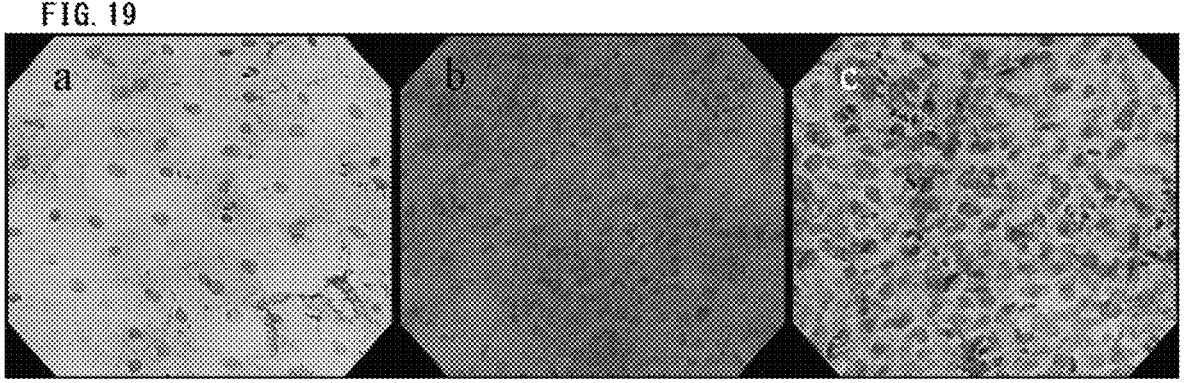
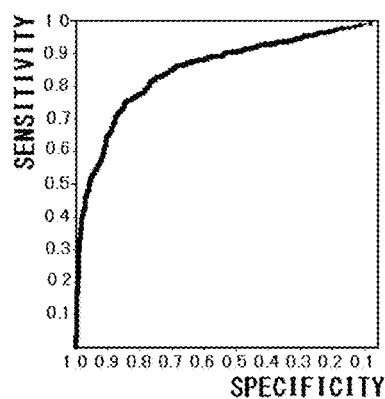
FIG. 20A
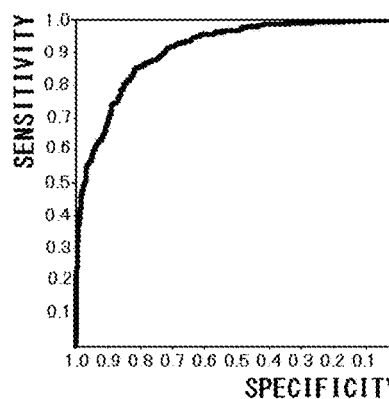
FIG. 20B
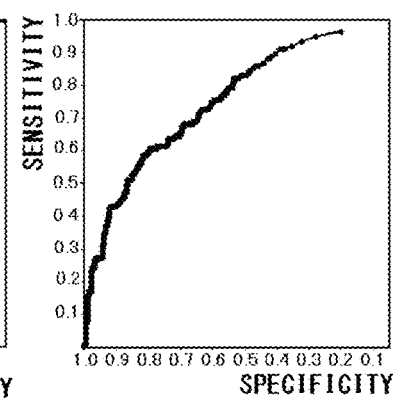
FIG. 20C

DISEASE DIAGNOSIS SUPPORT METHOD EMPLOYING ENDOSCOPIC IMAGES OF A DIGESTIVE ORGAN, A DIAGNOSIS SUPPORT SYSTEM, A DIAGNOSIS SUPPORT PROGRAM AND A COMPUTER-READABLE RECORDING MEDIUM HAVING THE DIAGNOSIS SUPPORT PROGRAM STORED THEREIN

A disease diagnosis support method employing endoscopic images of a digestive organ, a diagnosis support system, a diagnosis support program and a computer-readable recording medium having the diagnosis support program stored therein

RELATED APPLICATIONS

The present application is a National Phase of International Application No. PCT/JP2018/018316 filed May 11, 2018, which claims priority to Japanese Application Nos. 2017-114792, filed Jun. 9, 2017, and 2017-213311, filed Nov. 2, 2017.

FIELD

The present invention relates to a disease diagnosis support method employing endoscopic images of a digestive organ using a neural network, a diagnosis support system, a diagnosis support program and a computer-readable recording medium having the diagnosis support program stored therein.

BACKGROUND

Where endoscopic examination is performed in many cases for digestive organs such as a larynx, a pharynx, an esophagus, a stomach, a duodenum, a bile duct, a pancreatic duct, a small intestine, and a colon, endoscopic examination for upper digestive organs is often performed for screening of gastric cancer, esophageal cancer, peptic ulcer, and refluxed gastritis, and endoscopic examination for colon is often performed for screening colon cancer, colon polyp, colitis ulcerosa, and the like. In particular, endoscopic examination for upper digestive organs is also useful for the detailed examination of various epigastric symptoms, positive barium meal studies for gastric diseases, and abnormal serum pepsinogen levels, which are common components of a routine health check-up in Japan. Additionally, in recent years, conventional barium meal studies for gastric cancer screening have become increasingly replaced by gastroscopy.

Gastric cancer is one of the most common malignancies, with approximately one million cases estimated several years ago worldwide. Among the underlying causes of gastric cancer, *Helicobacter pylori* (hereinafter can be referred to as *H. pylori*), infection induces atrophic gastritis and intestinal metaplasia, eventually resulting in the development of gastric cancer. It is considered that *H. pylori* contributes to 98% of non-cardia gastric cancers worldwide. Given the increased risk of gastric cancer in *H. pylori*-infected patients, and the decreased incidence of gastric cancer following *H. pylori* eradication, the International Agency for Research on Cancer has classified *H. pylori* as a definite carcinogen. From this result, eradicating *H. pylori* is beneficial to reduce the risk of onset of gastric cancer. Eradication with an antibacterial agent is covered by medical service under health insurance in Japan and is strongly recommended treatment now and in the future from a viewpoint of sanitation.

To differential diagnosis for the presence of *H. pylori* infection, gastroscopy gives extremely useful information. While regular arrangement of collecting venules (RAC), in which blood capillaries are clearly seen, and fundic gland polyps are characteristic to gastric mucosa that is *H. pylori*-negative, atrophy, diffuse redness, mucosal swelling, and enlarged folds are representative findings for *H. pylori*-infected gastritis. An accurate endoscopic diagnosis of *H. pylori* infection will trigger confirmation by various tests such as blood or urine anti-*H. pylori* IgG levels measurement, fecal antigen test, urease breath test, or rapid urease test. Subsequently, patients with a positive test result are considered for *H. pylori* eradication. With endoscopic examination being widely used for the gastric disease screening, capability in identifying *H. pylori* infection during confirmation of gastric disease, without depending on the analysis of clinical samples, eliminates uniformly performed blood and urine tests, largely reduces burden on patients, and will contribute to medical economics.

Moreover, in particular in advanced industrial countries, disease rate of colitis ulcerosa (UC), is steadily increasing, and it is suggested that one of the causes for colitis ulcerosa is Western-style dietary life and environment. Several options for curing colitis ulcerosa include mesalazine, corticosteroid, and antitumor necrosis factor monoclonal antibody. It is significant to use these medications following clinical symptoms and disease activity index of patients so as to hold activated diseases in remission status.

In addition to scores of clinical symptoms, using colonoscopy of colitis ulcerosa patients, the degree and the severity of colitis ulcerosa are mainly evaluated. The previous studies reported a combination of the evaluation and measurement of disease activities with the endoscope. Among the combination, Mayo endoscopic score used to evaluate disease activities of colitis ulcerosa patients is one of the most reliable and widely used indexes. Specifically, Mayo endoscopic score is classified into the following four levels. That is, 0: normal or non-active, 1: mild (diffuse redness, unclear visible vascular pattern, mild easy bleeding), 2: moderate (marked diffuse redness, visible blood pattern extinction, easy bleeding, erosion), 3: heavy (natural bleeding, ulcer).

It is indicated that an endoscopic remission status that is defined as Mayo endoscopic score<1 and called "mucosal healing" correlates to lowering in corticosteroid usage rate, admission rate, clinical recurrence rate, and colectomy rate. However, according to reports until now, disease activity evaluation by non-endoscopists has substantial difference in κ-coefficient among observers, ranging from 0.45 to 0.53, and disease activity evaluation even by endoscopists has difference in the degree of matching with the κ-coefficient ranging from 0.71 to 0.74. It should be noted that the κ-coefficient is a parameter to evaluate the degree of matching for diagnosis among observers. A value of the parameter ranges from 0 to 1, and the degree of matching is determined to become higher as the value becomes greater.

During such endoscopic examination for the digestive organ, many endoscopic images are acquired. For the accuracy management, double checking of endoscopic images by endoscopists is obligated. With several tens of thousands of endoscopic examination annually performed, the number of images hourly read by one endoscopist in secondary reading is approximately 2,800. This number is huge and burdensome on site.

A diagnosis based on endoscopic images requires training for endoscopists, and is time-consuming in checking stored images. It is a subjective diagnosis and can cause false-positive and false-negative rates. Furthermore, fatigue of an endoscopist can adversely affect the diagnostic yield of this investigation. Such huge burden and lowered accuracy can lead to limitation in number of examinees, and give rise to concern that medical services meeting demand cannot be sufficiently provided.

In order to improve the endoscopic examination in the above-described workload and lowered accuracy, it is expected to make use of artificial intelligence (AI). Using AI the image recognition ability of which has exceeded that of human beings in these years as an assistant of endoscopists is expected to improve the accuracy and the speed of second reading.

Recent reports suggest that AI using deep learning has been remarked in various medical fields, the AI having the ability to screen medical images in areas including radiation oncology, skin cancer classification, and diabetic retinopathy, as a substitute for specialists in corresponding fields.

In particular, screening in micro-endoscope level has proved that AI is capable of providing accuracy equal to that with specialists (Non Patent Literature 1). Dermatologists have already released that AI having a deep learning function exerts the image diagnostic ability equal to that of the specialists (Non Patent Literature 2). Some patent documents use various types of machine learning methods (refer to Patent Literature 1 and Patent Literature 2). However, whether AI diagnostic ability for endoscopic images is able to satisfy the accuracy (precision) and the performance (speed) that are useful in actual medical front is yet validated, and diagnosis based on endoscopic images using machine learning has not been put into practice.

Deep learning is able to learn high-order feature values from input data by using a neural network that is composed of stacked multiple layers. Furthermore, deep learning is able to update internal parameters, by using a backpropagation algorithm, that are used to calculate respective representations of the layers from the representations in the previous layers, through indication of what change is to be made to a system.

Deep learning is capable of training association of medical images by using the previously stored medical images, and can be a strong machine-learning technique that allows users to acquire clinical characteristics of patients directly from the medical images. The neural network is a mathematical model in which characteristics of a brain neural circuit are represented with simulation on a computer, and is an approach of an algorithm that support deep learning.

CITATION LIST

Patent Literature

Patent Literature 1: Japanese Patent Application Laid-open No. 2017-045341
Patent Literature 2: Japanese Patent Application Laid-open No. 2017-067489
Patent Literature 3: Japanese Patent Application Laid-open No. 2013-113689

Non Patent Literature

Non Patent Literature 1: http://www.giejournal.org/article/S0016-5107(14), 02171-3/fulltext, "Novel computer-aided diagnostic system for colorectal lesions by using endocytoscopy" Yuichi Mori et al. Presented at Digestive Disease Week 2014, May 3-6, 2014, Chicago, Ill., USA
Non Patent Literature 2: "Nature" February, 2017, Opening article "Learning skin lesion: Artificial intelligence reinforces ability to detect skin cancer based on images" (http://www.natureasia.com/ja-jp/nature/highlights/82762),
Non Patent Literature 3: http://gentaikyo.or.jp/about/pdf/report/131119.pdf
Non Patent Literature 4: Kumagai Y, Monma K, Kawada K. "Magnifying chromoendoscopy of the esophagus: in-vivo pathological diagnosis using an endocytoscopy system.", Endoscopy, 2004, vol. 36, p 590-4.
Non Patent Literature 5: Esteva A, Kuprel B, Novoa R A, et al. "Dermatologist-level classification of skin cancer with deep neural networks", Nature, 2017, vol. 542, p 115-8.

SUMMARY

Technical Problem

In determination of endoscopic images in gastrointestinal endoscopic examination, promoting efficiency with high accuracy maintained has been largely demanded. Furthermore, when AI is to be used in image analysis in this field, improvement in the AI techniques is largely demanded. Furthermore, as far as the inventors know, there have been no reports regarding the ability of neural networks to diagnose *H. pylori*-infected gastritis, colitis ulcerosa, and esophageal disease, in particular, to diagnose esophageal disease using Endocytoscopy (ECS), images, and no examples in which the neural networks have been optimized to *H. pylori*-infected gastritis test, colitis ulcerosa test, and esophageal disease test, based on the analysis of these gastrointestinal endoscopic images, through deep learning, and implemented and used in medical front, which is a problem to be solved in future.

For upper endoscopy, images of not only a stomach but also a plurality of different organs such as a larynx, a pharynx, an esophagus, and a duodenum are acquired together in a mixed manner. In particular, for screening for gastric cancer through endoscopic examination, sorting the acquired images by organs or regions with AI can reduce burdens on endoscopists in writing remarks and second reading.

An object of the present invention is to provide a disease diagnosis support method employing endoscopic images of a digestive organ, a diagnosis support system, a diagnosis support program and a computer-readable recording medium having the diagnosis support program stored therein that are able to accurately diagnose diseases such as *H. pylori*-infected gastritis, colitis ulcerosa and esophageal diseases, by using endoscopic images of a digestive organ and using a neural network.

Solution to Problem

A disease diagnosis support method employing endoscopic images of a digestive organ according to a first aspect of the present invention is
a disease diagnosis support method employing endoscopic images of a digestive organ using a neural network, the method training a neural network by using
first endoscopic images of the digestive organ, and
corresponding to the first endoscopic images, at least one definitive diagnosis result of being positive or negative for a disease of the digestive organ, a past disease, a severity level, and information corresponding to an imaged region, the trained neural network outputting, based on second endoscopic images of the digestive organ, at least one of a probability of being positive and/or negative for the disease of the digestive organ, a probability of a past disease, a severity level of the disease, and the information corresponding to the imaged region.

With the disease diagnosis support method employing endoscopic images of a digestive organ using a neural network according to the first aspect, the neural network is trained based on first endoscopic images composed of endoscopic images of a plurality of digestive organs, which are obtained in advance for a plurality of corresponding subjects, and at least one definitive diagnosis result of being positive or negative for the disease, a past disease, a severity level, and information corresponding to an imaged region, which are each obtained in advance for each of the subjects, and thus it is possible to provide, in a short time with such accuracy that is substantially comparable to that with endoscopists, at least one of a probability of being positive and/or negative for the disease of the digestive organ of the subject, a probability of a past disease, a severity level of the disease, and the information corresponding to the imaged region, thereby making it possible to sort a subject who is to be separately subjected to definitive diagnosis. Furthermore, the diagnosis support method allows automated diagnosis for at least one of a probability of being positive and/or negative for a disease, a probability of a past disease, a severity level of the disease, and information corresponding to an imaged region, by comparing with test data composed of endoscopic images of a plurality of digestive organs of a large number of subjects. This automated diagnosis makes it easier for endoscopists to perform check and correction, and also reduce workload for creating sets of images associates with diseases.

A disease diagnosis support method employing endoscopic images of a digestive organ using a neural network according to a second aspect of the present invention is characterized in that, in a disease diagnosis support method system employing endoscopic images of a digestive organ using a neural network according to the first aspect, the first endoscopic images are adjusted in contrast.

With the disease diagnosis support method employing endoscopic images of a digestive organ using a neural network according to the second aspect, all of the first endoscopic images are adjusted in contrast so as to substantially have the same gray level, and thus the detection accuracy is improved in respective probabilities of being positive and being negative for a disease, and a severity level.

A disease diagnosis support method employing endoscopic images of a digestive organ using a neural network according to a third aspect of the present invention is characterized in that, in the disease diagnosis support method employing endoscopic images of a digestive organ using a neural network according to the first or the second aspect, the first endoscopic images are associated with respective imaged regions.

In some cases, with an untrained neural network, it is difficult to identify from what region a specific endoscopic image of a digestive organ was acquired. With the disease diagnosis support method employing endoscopic images of a digestive organ using a neural network according to the third aspect, the neural network is to be trained using endoscopic images classified by different regions, thereby making it possible to finely train the neural network according to different regions. Consequently, the neural network will improve in the detection accuracy with respect to the second endoscopic images regarding, for example, respective probabilities of being positive and being negative for a disease, a probability of a past disease, and a severity level of the disease.

A disease diagnosis support method employing endoscopic images of a digestive organ using a neural network according to a fourth aspect of the present invention is characterized in that, in the disease diagnosis support method employing endoscopic images of a digestive organ using a neural network according to the third aspect, the region includes at least one of a pharynx, an esophagus, a stomach, and a duodenum.

With the disease diagnosis support method employing endoscopic images of a digestive organ using a neural network according to the fourth aspect, classification by each region can be accurately performed for a pharynx, an esophagus, a stomach, and a duodenum, and thus the detection accuracy for each of the regions is improved in respective probabilities of being positive and being negative for a disease, a probability of a past disease, a severity level of the disease, and the like.

A disease diagnosis support method employing endoscopic images of a digestive organ using a neural network according to a fifth aspect of the present invention is characterized in that, in the disease diagnosis support method employing endoscopic images of a digestive organ using a neural network according to the third or the fourth aspect, the region is segmented in a plurality of portions for at least one of the digestive organs.

Because digestive organs each have a complicated shape, in some cases, with a small number of classifications for the region, it is difficult to recognize from what region a specific endoscopic image of a digestive organ was acquired. With the disease diagnosis support method employing endoscopic images of a digestive organ using a neural network according to the fifth aspect, digestive organs are each segmented in a plurality of portions, thereby making it possible to provide a high-accuracy diagnosis result in a short time.

A disease diagnosis support method employing endoscopic images of a digestive organ using a neural network according to a sixth aspect of the present invention is characterized in that, in the disease diagnosis support method employing endoscopic images of a digestive organ using a neural network according to the fifth aspect, when the region is of a stomach, the segments include at least one of an upper stomach, a middle stomach, and a lower stomach. A disease diagnosis support method employing endoscopic images of a digestive organ using a neural network according to a seventh aspect of the present invention is characterized in that, in the disease diagnosis support method employing endoscopic images of a digestive organ using a neural network according to the fifth aspect, when the region is of a stomach, the segments include at least one of a cardia, a gastric fundus, a gastric corpus, an angular region, an antral zone, an antrum, and a pylorus.

With the disease diagnosis support method employing endoscopic images of a digestive organ using a neural network according to the sixth or the seventh aspect of the present invention, classification by each segment or region can be accurately performed for a stomach, and thus the detection accuracy for each of the segments or the regions is improved in respective probabilities of being positive and being negative for a disease, a probability of a past disease, a severity level of the disease, and the like. It should be noted that selection between the segments and the regions may be made as appropriate according to necessities.

A disease diagnosis support method employing endoscopic images of a digestive organ using a neural network according to an eighth aspect of the present invention is characterized in that, in the disease diagnosis support method employing endoscopic images of a digestive organ using a neural network according to any one of the third to the seventh aspects, when the number of the first endoscopic images in one of the imaged regions is smaller than that in another region, by using at least one of rotation, enlargement, reduction, change in the number of pixels, extraction of bright and dark portions, and extraction of portions having change in hue, for the first endoscopic images, the number of the first endoscopic images is made substantially equal in every region.

In some cases, the number of first endoscopic images composed of endoscopic images of a plurality of digestive organs, which have been obtained in advance for a plurality of corresponding subjects are largely different for different regions. With the disease diagnosis support method employing endoscopic images of a digestive organ using a neural network according to the eighth aspect, also in such a case, by using at least one of rotation, enlargement, reduction, change in the number of pixels, extraction of bright and dark portions, and extraction of portions having change in hue, for the first endoscopic images of a certain region, it is possible to increase the number of pixels for training the neural network, thereby reducing variation in the detection accuracy, which is caused by difference in the regions, in respective probabilities of being positive and being negative for a disease, a probability of a past disease, a severity level of the disease, and the like. It should be noted that in the disease diagnosis support method employing endoscopic images of a digestive organ using a neural network according to the eighth aspect, the number of endoscopic images for each region does not always need to be the same, but it is sufficient that variation in number is reduced.

A disease diagnosis support method employing endoscopic images of a digestive organ using a neural network according to a ninth aspect of the present invention is characterized in that, in the disease diagnosis support method employing endoscopic images of a digestive organ using a neural network according to any one of the third to the eighth aspects, the trained neural network is capable of outputting information corresponding to a region at which the second endoscopic images have been imaged.

Normally, many endoscopic images or continuously captured images of digestive organs are obtained for one subject. With the disease diagnosis support method employing endoscopic images of a digestive organ using a neural network according to the ninth aspect, respective probabilities of being positive and being negative for a disease and a region name are output for each of the second endoscopic images, thereby making it easy to grasp regions at which the disease is positive and distribution of the regions.

A disease diagnosis support method employing endoscopic images of a digestive organ using a neural network according to a tenth aspect of the present invention is characterized in that, in the disease diagnosis support method employing endoscopic images of a digestive organ using a neural network according to the ninth aspect, the trained neural network outputs the probabilities or the severity level together with information corresponding to the region.

With the disease diagnosis support method employing endoscopic images of a digestive organ using a neural network according to the tenth aspect, the probabilities or the severity, and region names are output in a descending order of probabilities of being positive of a disease and a severity level, thus making it easy to grasp regions to be accurately examined.

A disease diagnosis support method employing endoscopic images of a digestive organ using a neural network according to an eleventh aspect of the present invention is characterized in that, in the disease diagnosis support method employing endoscopic images of a digestive organ using a neural network according to any one of the first to the tenth aspects, the first endoscopic images include gastroscopic images, and the disease includes at least one of with or without *H. pylori* infection and with or without *H. pylori* eradication.

With the disease diagnosis support method employing endoscopic images of a digestive organ using a neural network according to the eleventh aspect, it is possible to predict respective probabilities of being positive and being negative of *H. pylori* infection of a subject and with or without *H. pylori* eradication, with accuracy equal to that with Board Certified Gastroenterologists of the Japanese Gastroenterological Endoscopy Society, thereby making it possible to accurately select in a short time a subject to be separately subjected to definitive diagnosis. It should be noted that the definitive diagnosis can be performed to a selected subject through blood or urine anti-*H. pylori* IgG levels measurement, fecal antigen tests, or urease breath tests.

A disease diagnosis support method employing endoscopic images of a digestive organ using a neural network according to a twelfth aspect of the present invention is characterized in that, in the disease diagnosis support method employing endoscopic images of a digestive organ using a neural network according to any one of the first to the tenth aspects, the first endoscopic images include colon fiberscope images, the disease includes at least colitis ulcerosa, and the trained neural network outputs a result after being segmented in a plurality of stages according to the severity level of the colitis ulcerosa.

With the disease diagnosis support method employing endoscopic images of a digestive organ using a neural network according to the twelfth aspect, it is possible to the predict severity level of colitis ulcerosa of a subject with accuracy equal to that with the Board Certified Gastroenterologists of the Japanese Gastroenterological Endoscopy Society, thereby making it possible to accurately select in a short time a subject to be separately subjected to additional close examination.

A disease diagnosis support method employing endoscopic images of a digestive organ using a neural network according to a thirteenth aspect of the present invention is characterized in that, in the disease diagnosis support method employing endoscopic images of a digestive organ using a neural network according to any one of the first to the tenth aspects, the first endoscopic images include esophagus endoscopic images with Endocytoscopy, the disease includes at least one of esophageal cancer, gastroesophageal reflux disease, and esophagitis, and the trained neural network outputs a result after being segmented, for at least one of the esophageal cancer, the gastroesophageal reflux disease, and the esophagitis.

With the disease diagnosis support method employing endoscopic images of a digestive organ using a neural network according to the thirteenth aspect, it is possible to minimize overdiagnosis, in which a non-cancerous lesion is diagnosed cancerous based on esophagus endoscopic images with Endocytoscopy, thereby making it possible to reduce the number of subjects to be subjected to tissue biopsy.

A disease diagnosis support method employing endoscopic images of a digestive organ using a neural network according to a fourteenth aspect of the present invention is characterized in that, in the disease diagnosis support method employing endoscopic images of a digestive organ using a neural network according to any one of the first to the thirteenth aspects, the second endoscopic images are at least one of images that are being captured with an endoscope, images transmitted via a communication network, images to be provided from a remote operation system or a cloud system, images stored in a computer-readable recording medium, and moving images.

With the disease diagnosis support method employing endoscopic images of a digestive organ according to the fourteenth aspect, it is possible to output, in a short time, respective probabilities of being positive and being negative or a severity level for a disease of a digestive organ with respect to the second endoscopic images that were input, thereby making it possible to use images transmitted from a remote site, for example, and moving images, regardless of the input format of the second endoscopic images.

It should be noted that available communication networks include the Internet that is well known, intranet, extranet, LAN, ISDN, VAN, CATV communication networks, virtual private networks, telephone networks, mobile communication networks, and satellite communication networks. Moreover, available transmission media constituting communication networks include wired media such as the IEEE1394 serial bus that is well known, USB, power line communication, cable TV circuit, telephone line circuit, and ADSL circuit, and wireless media such as infrared radiation, Bluetooth (registered trademark), IEEE802.11, mobile telephone network, satellite circuit, and terrestrial digital network. These communication networks and media allow the diagnosis support system to be used in forms of what is called cloud service and a remote support service.

Available computer-readable storage media include tape based media that are well known, such as magnetic tapes and cassette tapes, disc based media including floppy (registered trademark) disks, magnetic discs such as hard discs, optical discs such as compact discs (CD)-ROM, MO, MD, digital video discs, and compact disc-R, card based media such as IC cards, memory cards, and optical cards, and semiconductor memory based media such as mask ROM, EPROM, EEPROM, and flash ROM. These computer-readable storage media provide a form in which the system can be easily implanted and installed in what is called medical institution and health examination institution.

A disease diagnosis support method employing endoscopic images of a digestive organ using a neural network according to a fifteenth aspect of the present invention is characterized in that, in the disease diagnosis support method employing endoscopic images of a digestive organ using a neural network according to any one of the first to the fourteenth aspects, a convolutional neural network is used as the neural network.

The convolutional neural network serving as a neural network is a mathematical model in which brain characteristics in a visual cortex are simulated, and is extremely excellent in the ability of learning images. Thus, the disease diagnosis support method employing endoscopic images of a digestive organ using a neural network according to the fifteenth aspect has higher sensitivity and higher specificity, thereby providing extremely large benefits.

A disease diagnosis support system employing endoscopic images of a digestive organ according to a sixteenth aspect of the present invention is a disease diagnosis support system employing endoscopic images of a digestive organ including an endoscopic image input unit, an output unit, and a computer having a neural network embedded therein. The computer includes a first storage area having first endoscopic images of a digestive organ stored therein, a second storage area having, corresponding to the first endoscopic images, at least one definitive diagnosis result stored therein, the result being positive or negative for the disease of the digestive organ, a past disease, a severity level, and information corresponding to an imaged region, and a third storage area having the neural network program stored therein. The neural network program is trained based on the first endoscopic images stored in the first storage area and the definitive diagnosis result stored in the second storage area, and outputs, based on second endoscopic images of the digestive organ input from the endoscopic image input unit, at least one of a probability of being positive and/or negative for the disease of the digestive organ with respect to the second endoscopic images, a probability of a past disease, a severity level of the disease, and information corresponding to the imaged region.

A disease diagnosis support system employing endoscopic images of a digestive organ according to a seventeenth aspect of the present invention is characterized in that, in the disease diagnosis support system employing endoscopic images of a digestive organ according to the sixteenth aspect, the training/validation data are adjusted in contrast.

A disease diagnosis support system employing endoscopic images of a digestive organ according to an eighteenth aspect of the present invention is characterized in that, in the disease diagnosis support system employing endoscopic images of a digestive organ according to the sixteenth or the seventeenth aspect, the first endoscopic images are each associated with an imaged region.

A disease diagnosis support system employing endoscopic images of a digestive organ according to a nineteenth aspect of the present invention is characterized in that, in the disease diagnosis support system employing endoscopic images of a digestive organ according to the eighteenth aspect, the region includes at least one of a pharynx, an esophagus, a stomach, and a duodenum.

A disease diagnosis support system employing endoscopic images of a digestive organ according to a twentieth aspect of the present invention is characterized in that, in the disease diagnosis support system employing endoscopic images of a digestive organ according to the eighteenth or the nineteenth aspect, the region is segmented in a plurality of portions for at least one of the digestive portions.

A disease diagnosis support system employing endoscopic images of a digestive organ according to a twenty-first aspect of the present invention is characterized in that, in the disease diagnosis support system employing endoscopic images of a digestive organ according to the twentieth aspect, when the region is of a stomach, the segments include at least one of an upper stomach, a middle stomach, and a lower stomach.

A disease diagnosis support system employing endoscopic images of a digestive organ according to a twenty-second aspect of the present invention is characterized in that, in the disease diagnosis support system employing endoscopic images of a digestive organ according to the twentieth aspect, when the region is of a stomach, the segments include at least one of a cardia, a gastric fundus, a gastric corpus, an angular region, an antral zone, an antrum, and a pylorus.

A disease diagnosis support system employing endoscopic images of a digestive organ according to a twenty-third aspect of the present invention is characterized in that, in the disease diagnosis support system employing endoscopic images of a digestive organ according to any one of the sixteenth to the twenty-second aspects, when the number of the first endoscopic images in one of the imaged regions is smaller than that in another region, by using at least one of rotation, enlargement, reduction, change in the number of pixels, extraction of bright and dark portions, and extraction of portions having change in hue, for the first endoscopic images, the number of pieces of training/validation data is made substantially equal in every region.

A disease diagnosis support system employing endoscopic images of a digestive organ according to a twenty-fourth aspect of the present invention is characterized in that, in the disease diagnosis support system employing endoscopic images of a digestive organ according to any one of the sixteenth to the twenty-third aspects, the trained neural network program is capable of outputting information corresponding to a region at which the second endoscopic images have been imaged.

A disease diagnosis support system employing endoscopic images of a digestive organ according to a twenty-fifth aspect of the present invention is characterized in that, in the disease diagnosis support system employing endoscopic images of a digestive organ according to the twenty-fourth aspects, the trained neural network program outputs the probabilities and the severity level together with the information corresponding to the region.

A disease diagnosis support system employing endoscopic images of a digestive organ according to a twenty-sixth aspect of the present invention is characterized in that, in the disease diagnosis support system employing endoscopic images of a digestive organ according to any one of the sixteenth to the twenty-fifth aspects, the first endoscopic images include gastroscopic images, and the disease includes at least one of with or without *H. pylori* infection with or without *H. pylori* eradication.

A disease diagnosis support system employing endoscopic images of a digestive organ according to a twenty-seventh aspect of the present invention is characterized in that, in the disease diagnosis support system employing endoscopic images of a digestive organ according to any one of the sixteenth to the twenty-fifth aspects, the first endoscopic images include colon fiberscopic images, the disease includes at least colitis ulcerosa, and the trained neural network program outputs a result after being segmented in a plurality of stages according to the severity level of the colitis ulcerosa.

A disease diagnosis support system employing endoscopic images of a digestive organ according to a twenty-eighth aspect of the present invention is characterized in that, in the disease diagnosis support system employing endoscopic images of a digestive organ according to any one of the sixteenth to the twenty-fifth aspects, the first endoscopic images include esophagus endoscopic images with Endocytoscopy, the disease includes at least one of esophageal cancer, gastroesophageal reflux disease, and esophagitis, and the trained neural network outputs a result after being segmented, for at least one of the esophageal cancer, the gastroesophageal reflux disease, and the esophagitis.

A disease diagnosis support system employing endoscopic images of a digestive organ according to a twenty-ninth aspect of the present invention is characterized in that, in the disease diagnosis support system employing endoscopic images of a digestive organ according to any one of the sixteenth to the twenty-eighth aspects, the second endoscopic images are at least one of images that are being captured with an endoscope, images transmitted via a communication network, images to be provided from a remote operation system or a cloud system, images stored in a computer-readable recording medium, and moving images.

A disease diagnosis support system employing endoscopic images according to a thirtieth aspect of the present invention is characterized in that, in the disease diagnosis support system employing endoscopic images of a digestive organ according to any one of the sixteenth to the twenty-ninth aspects, the neural network is a convolutional neural network.

With the disease diagnosis support system employing endoscopic images of a digestive organ using a neural network according to any one of the sixteenth to the thirtieth aspects, it is possible to exert the same effect as that with the disease diagnosis support method employing endoscopic images of a digestive organ according to any one of the first to the fifteenth aspects.

A diagnosis support program based on endoscopic images of a digestive organ according to a thirty-first aspect of the present invention is a product that causes a computer to operate as means in the disease diagnosis support system employing endoscopic images of a digestive organ according to any one of the sixteenth to the thirtieth aspects.

With the diagnosis support program based on endoscopic images of a digestive organ according to the thirty-first aspect of the present invention, it is possible to provide a diagnosis support program based on endoscopic images of a digestive organ, in which the program causes a computer to operate as means in the disease diagnosis support system employing endoscopic images of a digestive organ according to any one of the sixteenth to the thirtieth aspects.

A diagnosis support program based on endoscopic images of a digestive organ according to a thirty-second aspect of the present invention has the diagnosis support program based on endoscopic images of a digestive organ according to the thirty-first aspect stored therein.

With the diagnosis support program based on endoscopic images of a digestive organ according to the thirty-second aspect of the present invention, it is possible to provide a computer-readable storage medium having the diagnosis support program stored therein based on endoscopic images of a digestive organ according to the thirty-first aspect.

A region determination method for a digestive organ employing endoscopic images of the digestive organ using a neural network according to a thirty-third aspect of the present invention is a region determination method for a digestive organ employing endoscopic images of the digestive organ using a neural network, the determination method including training the neural network by using first endoscopic images of the digestive organ and definitive information, corresponding to the first endoscopic images, on information corresponding to an imaged region, the trained neural network outputting, based on second endoscopic images of the digestive organ, information corresponding to the imaged region of the digestive organ.

With the region determination method for a digestive organ employing endoscopic images of the digestive organ using a neural network according to the thirty-third aspect of the present invention, the neural network is trained by using first endoscopic images of a digestive organ and definitive information, corresponding to the first endoscopic images, on information corresponding to the imaged region, and thus, it is possible to provide in a short time information corresponding to an imaged region of a subject with accuracy substantially comparable to that with endoscopists, and determine in short time a region of a digestive organ that is a diagnosis target. Furthermore, the determination method allows auto determination for information corresponding to an imaged region, by comparing with test data composed of a plurality of endoscopic images of a digestive organ of a large number of subjects. This automated determination makes it easier for endoscopists to perform check or the like, and also reduce workload for analyzing images associates with diseases.

A region determination system for a digestive organ employing endoscopic images of the digestive organ using a neural network according to a thirty-fourth aspect of the present invention is a region determination system for a digestive organ employing endoscopic images of the digestive organ, the determination system including an endoscopic image input unit, an output unit, and a computer having a neural network embedded therein. The computer includes a first storage area having first endoscopic images of a digestive organ stored therein, a second storage area having definitive information, corresponding to the first endoscopic images, on information corresponding to an imaged region of the digestive organ stored therein, and a third storage area having the neural network program stored therein. The neural network program is trained based on the first endoscopic images stored in the first storage area and the definitive information stored in the second storage area, and outputs, based on second endoscopic images of the digestive organ input from the endoscopic image input unit, information corresponding to the imaged region of the digestive organ with respect to the second endoscopic images.

With the region determination system for a digestive organ employing endoscopic images of the digestive organ using a neural network according to a thirty-fourth aspect of the present invention, it is possible to exert the same effect as that with the region determination method for a digestive organ employing endoscopic images of the digestive organ using a neural network according to the thirty-third aspect.

A region determination program for a digestive organ employing endoscopic images of the digestive organ according to a thirty-fifth aspect of the present invention is a product for a computer to operate as means in the region determination system for a digestive organ employing endoscopic images of the digestive organ according to the thirty-fourth aspect.

With the region determination program for a digestive organ employing endoscopic images of the digestive organ according to the thirty-fifth aspect of the present invention, it is possible to provide a region determination system for a digestive organ employing endoscopic images of the digestive organ for a computer to operate as means in the region determination system for a digestive organ employing endoscopic images of the digestive organ according to the thirty-fourth aspect.

A computer-readable recording medium according to a thirty-sixth aspect of the present invention has the region determination program for a digestive organ employing endoscopic images of the digestive organ according to the thirty-fifth aspect stored therein.

With the computer-readable recording medium according to a thirty-sixth aspect of the present invention, it is possible to provide a computer-readable recording media having the region determination program for a digestive organ employing endoscopic images of the digestive organ according to the thirty-fifth aspect stored therein.

Advantageous Effects of Invention

As in the foregoing, with the present invention, a computer program having a neural network embedded therein is trained based on a plurality of endoscopic images of digestive organs, which are obtained in advance for a plurality of corresponding subjects, and definitive diagnosis results of being positive or negative for the disease, which are obtained in advance for the corresponding subjects, and thus it is possible to provide, in a short time with such accuracy that is substantially comparable to that with endoscopists, a probability of being positive and/or negative for the disease of the digestive organ of the subject, a probability of a past disease, a severity level of the disease, the information corresponding to the imaged region, and the like, thereby making it possible to sort in a short time a subject who is to be separately subjected to definitive diagnosis.

BRIEF DESCRIPTION OF DRAWINGS

FIG. 1A is an example of gastroscopic images of a *H. pylori* positive subject;

FIG. 1B is an example of gastroscopic images of a *H. pylori* negative subject;

FIG. 2 is a diagram illustrating sorting of patients so as to prepare test data sets;

FIG. 18 is a diagram illustrating an example of low-magnification images (a to e), and high-magnification images (f to j), according to a fourth embodiment;

FIG. 19 is a diagram illustrating an example of images that are classified into Type 1 (FIG. 19A), Type 2 (FIG. 19B), and Type 3 (FIG. 19C), respectively according to the fourth embodiment;

FIG. 20A is a diagram illustrating an ROC curve for all of the images in the fourth embodiment;

FIG. 20B is a diagram illustrating an ROC curve for HMP;

FIG. 20C is a diagram illustrating an ROC curve for LMP;

FIG. 21 illustrates an example of images where the CNN of the fourth embodiment misdiagnoses as non-malignancy;

FIG. 22 is a diagram illustrating an example of images where an endoscopist misdiagnoses as malignancy;

DESCRIPTION OF EMBODIMENTS

Figure 3:
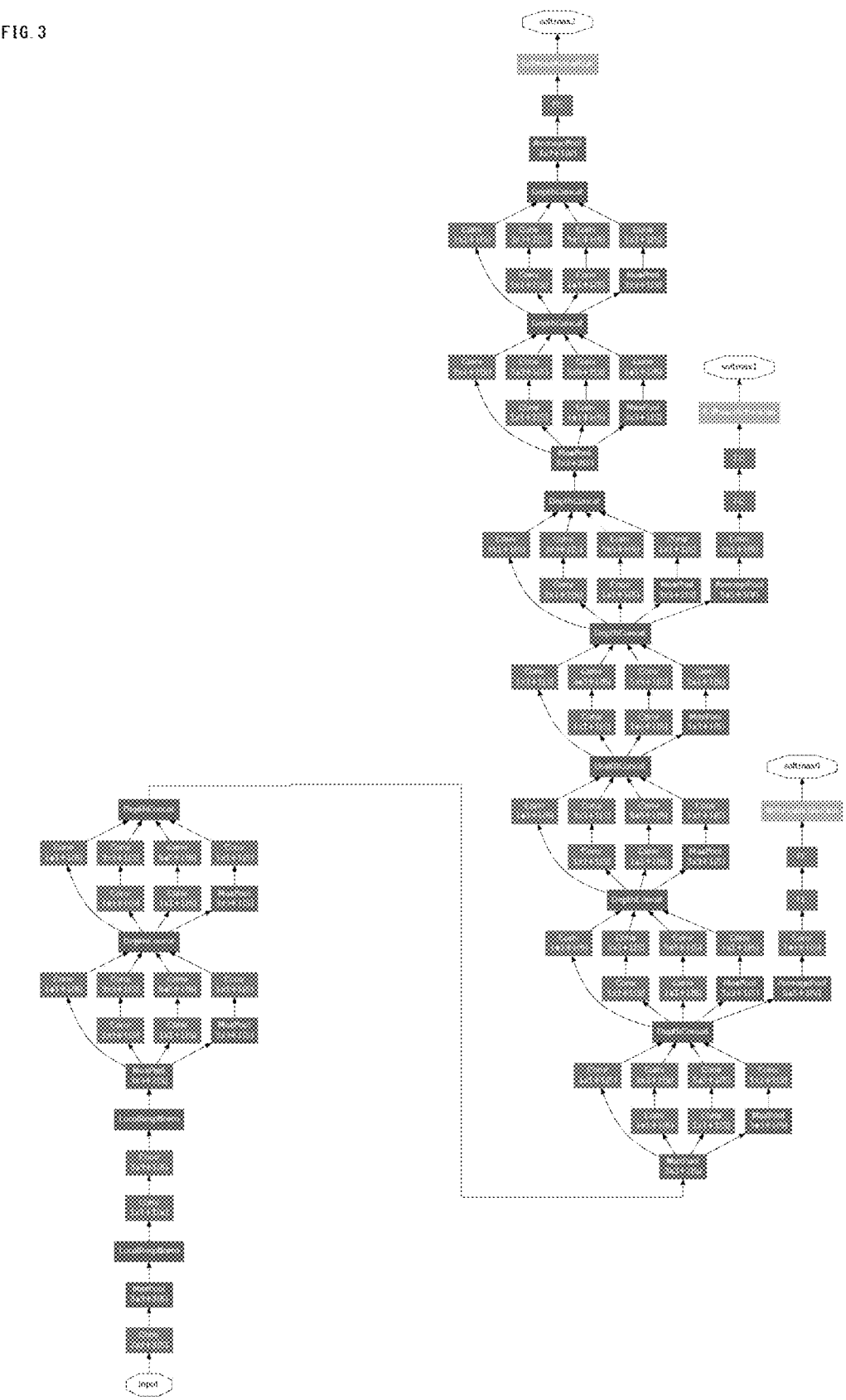
FIG. 3 is a schematic diagram illustrating operations of GoogLeNet.

The following describes in detail a disease diagnosis support method employing endoscopic images of a digestive organ, a diagnosis support system, a diagnosis support program and a computer-readable recording medium having the diagnosis support program stored therein, according to the present invention, first by taking cases of H. pylori-infected gastritis and classification by organs as examples, and then taking cases of colitis ulcerosa and esophageal diseases as next examples. However, embodiments described below indicate examples to embody technical thought of the present invention, but not intend to limit the present invention to these embodiments. That is, the present invention extends to general diseases specifiable with endoscopic images of digestive organs, and is equally applicable to matters in other embodiments included in the claims. Furthermore, in the present invention, a term, image includes not only a static image but also a moving image.

First, with reference to a quadrant table listed in Table 1, accuracy of general tests, the sensitivity, and the specificity will be briefly explained. Generally, test values are continuous amounts, and thus, determination is performed such that a value higher than a cut-off point (threshold) is positive, and a value lower than the cut-off point is negative (this may be opposite).

TABLE 1

| | | Disease | |
|---|---|---|---|
| | | With | Without |
| Test results | positive | a true positive | b false positive |
| | negative | c false negative | d true negative |

Sensitivity = a/ (a + c)

Specificity = d/ (b + d)

As listed in Table 1, depending on presence or absence of a disease of a patient and a test result being positive or negative for a disease, the patient is classified into one of four areas, a to d. It should be noted that, a patient having a disease is classified into with disease (with) and a patient having no disease is classified into without disease (without). Patients in an area a have a disease and the test results are positive, which means the area a is a true positive area. Patients in an area b have no disease, but the test results are positive, which means the area b is a false positive area. Patients in an area c have a disease and the test results are negative, which means the area c is a false negative area. Patients in an area d have no disease and the test results are negative, which means the area d is a true negative area.

By contrast, the sensitivity is a probability that the test result of a patient having a disease is positive (specificity true positive rate), and is expressed as a/(a+c). The specificity is a probability that the test result of a patient having no disease is negative (specificity true negative rate), and is expressed as d/(b+d). It should be noted that the false-positive rate is a probability that the test result of a patient having no disease is positive (specificity false negative rate), and is expressed as b/(b+d). The false-negative rate is a probability that the test result of a patient having a disease is negative (specificity false positive rate), and is expressed as c/(a+c).

Figure 4:
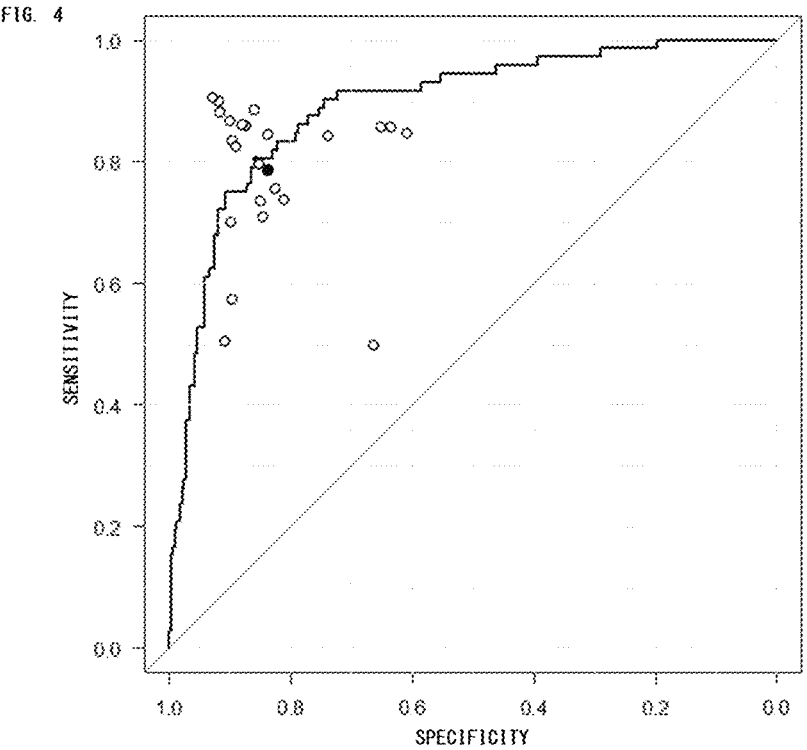
FIG. 4 is a diagram illustrating a receiver operating characteristic (ROC) curve, the curve representing first learning results and *H. pylori* infection diagnosis results by an endoscopic examiner.
Figure 5:
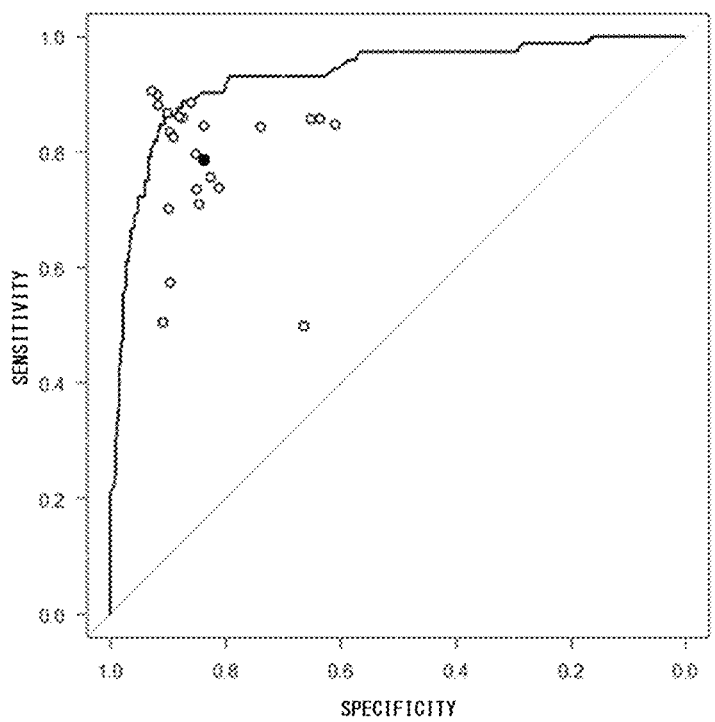
FIG. 5 is a diagram illustrating an ROC curve representing second execution results and *H. pylori* infection diagnosis results by an endoscopic examiner.

Furthermore, where the sensitivity and the specificity are calculated each time the cut-off value is changed, and the calculated values are plotted with the abscissa representing the sensitivity and the ordinate representing the false-positive rate (=1-specificity), an ROC curve (Receiver Operating Characteristic: receiver operation characteristic curve) is provided (refer to FIG. 4 and FIG. 5).

First Embodiment

A first embodiment describes a case in which a disease diagnosis support method employing endoscopic images, a diagnosis support system, a diagnosis support program and a computer-readable recording medium having the diagnosis support program stored therein, which are of the present invention, are applied to the case of *H. pylori*-infected gastritis. A total of 33 endoscopic examiners performed esophagogastroduodenoscopy (hereinafter referred to as "EGD") using an endoscope at regular magnification with white light at a clinic to which one of the inventors belongs. The indications for EGD were referral from a primary care physician for evaluation of various epigastric symptoms, positive results from gastric disease screening by barium meal, abnormal serum pepsinogen levels, a previous history of gastroduodenal disease, or screening. All the endoscopists were directed to image overall pictures of a larynx, an esophagus, a stomach, and a duodenum even if no abnormality is observed. The typical number of images of patients without gastrointestinal disease was 34 (larynx: 1, esophagus: 6, Stomach: 25, and duodenum: 2).

We used standard endoscopes (such as EVIS GIF-XP290N, GIF-XP260, GIF-XP260NS, GIF-N260, and the like; Olympus Medical Systems, Co., Ltd., Tokyo, Japan) to capture images, using white light, so as to perform EGD therefor. The obtained images are images having regular magnification, and we did not use magnified images in this study. FIG. 1 shows the typical gastric-endoscopic images. It should be noted that FIG. 1A shows an example image that was diagnosed as *H. pylori*-positive, and FIG. 1B is an example image that was diagnosed as *H. pylori*-negative.

All the included patients were tested for *H. pylori* infection by at least one of the following tests: blood or urine anti-*H. pylori* IgG levels measurement, fecal antigen measurement, and urease breath test. Patients who tested positive on any of these assays were classified as *H. pylori*-positive. Among patients who were not classified as *H. pylori*-positive, those who had no history of *H. pylori* eradication were classified as *H. pylori*-negative. Patients who successfully underwent *H. pylori* eradication were excluded from the measurement target.

[Regarding Data Set]

We prepared a data set (referred to as "training/validation data") to be used to educate and construct the AI-based diagnostic system by retrospectively reviewing the images of EGD performed for 1768 cases from January 2014 to December 2016. Patients with the presence or the history of gastric cancer, ulcer, or submucosal tumor were excluded from the training/validation data set. Some of the images of the stomach diagnosed as *H. pylori*-positive or *H. pylori*-negative were excluded by endoscopists for various reasons including food residue in the stomach, bleeding following biopsy, and halation. We also prepared a data set of endoscopic images that are to be evaluation target (referred to as "test data"). It should be noted that this "training/validation data" corresponds to the "first endoscopic images" of the present invention, and the "test data" corresponds to the "second endoscopic images" of the present invention. Table 2 shows the demographical characteristics of patients and the characteristics of the images.

TABLE 2

| | | Training/validation data set | Test data set |
|---|---|---|---|
| Number of images | | 32,208 | 11,481 |
| Number of endoscopists | | 33 | 13 |
| Number of patients | | 1768 | 397 |
| Patient age (SD (years)) | | 52.7 (13.2) | 50.4 (11.2) |
| Patient gender | Male (%) | 480 (45) | 168 (43) |
| | Female (%) | 598 (55) | 226 (57) |
| *H. pylori* diagnosis result | Positive | 753 (43) | 73 (18) |
| | Negative | 1,015 (57) | 335 (82) |

SD: standard deviation

As shown in Table 2, we prepared a training/validation data set consisting of 32,208 sheets by using images from 753 patients determined as *H. pylori*-positive and 1,015 patients classified as negative. In this data set, RGB signals are adjusted so as to provide the same contrast ratio to all the images. With the RGB colors each having 8 bits, that is, the values of which each ranging from 0 to 255 bits, the images were adjusted in contrast so that the image includes at least one white point, at which respective values of the RGB colors are 255, 255, 255 (white color). Normally the quality of endoscopic images is favorable, and thus actually in many cases, the endoscopic images were not adjusted in contrast. The endoscope has a screen with a black frame. On the screen, automated cropping was performed for enlargement and reduction of an image, so that all the images had the same size.

For classification, digestive organs may be each segmented in a plurality of portions. In the first embodiment, only for a stomach, images were obtained to be classified into a plurality of portions according to their location in the stomach, and for the other regions, images were used as they were without being segmented.

Furthermore, with data being input by attributes such as gender and ages, diagnosis can be performed for each attribute.

It is ideal to obtain equal number of pieces of data for every classification. However, for classification with a smaller number of pieces of data, images were rotated between 0 and 359 degrees and enlarged or reduced as appropriate with a certain tool, so as to increase pieces of data in number. As a result, we obtained 32,208 original endoscopic images for training/validation.

First, the first construction of a neural network was performed with all images combined without including classified data. Next, the second construction of the neural network was performed using images classified into a plurality of portions as described above. It should be noted that the construction of these neural networks had a lot of iterative processing, and a computer accelerated with parallel processing was used.

[Preparing Test Data]

To evaluate the diagnostic accuracy of the neural network constructed using the above-described training/validation data set in the first embodiment, and to compare it with endoscopic examiners, a test data set was prepared. Among image data from 587 patients who underwent endoscopic examination from January to February 2017 at a clinic to which one of the inventors belongs, image data from 166 patients who completed *H. pylori* eradication, image data from 23 patients having unknown *H. pylori* infection status, and image data from one patient who underwent gastrectomy (refer to FIG. 2). As a result, image data from the remaining 397 patients determined to be *H. pylori*-positive or *H. pylori*-negative for a disease was used as test data.

The diagnosis was established by fecal antigen test in 72 (43%), and urine anti-*H. pylori* IgG levels in 87 (21%). The test data set included a total of 11,481 images from 397 patients, out of which 72 patients are diagnosed as *H. pylori*-positive, and 325 patients as *H. pylori*-negative. There was no overlap between the test and the training/validation data set.

[Training Algorithm]

To construct an AI-based diagnostic system, making use of a Caffe framework as development infrastructure of the deep learning neural network, we used GoogLeNet that consists of 22 layers as the convolutional neural network (CNN) architecture.

The CNN used in the first embodiment is trained by using backpropagation as illustrated in FIG. 3. All layered of the CNN were fine-tuned by using Adam (https://arxiv.org/abs/1412.6980), a method for parameter optimization with a global learning rate of 0.0001.

To optimize all images for GoogLeNet, each image was resized to 244×244 pixels. We used a pre-trained model that learned natural-image features through ImageNet. ImageNet (http://www.image-net.org/) is a database having 14 million or more images stored therein in the beginning of 2017. This training procedure, known as transfer learning, is useful even with sparse training data.

[Evaluation Algorithm]

The trained neural network outputs a probability score (PS) between 0 and 1 as a diagnosis result for *H. pylori* being positive or *H. pylori* being negative for a disease, corresponding to the input image. Receiver operating characteristic (ROC) curves were made by plotting the PS by varying the threshold to identify being positive or negative for a disease.

[Comparison Between CNN and Endoscopic Examiners on Performance of Test Data Sets]

Patients were classified as *H. pylori*-positive or *H. pylori*-negative for a disease based on their endoscopic images respect to the test data sets by 23 endoscopic examiners having experiences of CNN and EGD. Furthermore, the accuracy of *H. pylori* infection diagnosis and a time needed for evaluation were measured, and the measurements were compared between the CNN and the endoscopists.

Six of the 23 endoscopic examiners are the Board Certified Gastroenterologists of the Japanese Gastroenterological Endoscopy Society. The other 17 endoscopists, who have experience of EGD, are further classified as: endoscopists having performed for more than 1,000 patients (n=9), classified as a "relatively experienced group", and endoscopists having performed for less than 1,000 patients (n=8), classified as a "beginners group". The ROC curve with which the diagnostic accuracy of the CNN is displayed was described by using the R software (statistical analysis free software). Information on all the patients displayed on these images was de-identified prior to the data analyses for maintaining patient anonymity. Information on identifiable patients was not accessible to any of the endoscopic examiners involved in the evaluation. This study was approved by the Institutional Review Board of the Japan Medical Association (ID JMA-IIA00283).

[Results from Endoscopic Examiners]

Table 3 shows the sensitivity, the specificity, and the time needed for evaluation on the diagnosis of *H. pylori* infection by the endoscopic examiners. The average sensitivity and the average specificity of all the endoscopic examiners were 79.6% and 83.2%, respectively. The time needed to evaluate all the images of the test data sets (evaluation time) was 230±65 (average±standard deviation (SD)) min.

TABLE 3

| | Number of endoscopists | Sensitivity (SD) (%) | Specificity (SD) (%) | Accuracy (SD) (%) | AUC | Time (SD) (min) |
|---|---|---|---|---|---|---|
| Primary | — | 81.9 | 83.4 | 83.1 | 0.89 | 3.3 |
| Secondary | — | 88.9 | 87.4 | 87.7 | 0.93 | 3.2 |
| Certified endoscopists | 6 | 85.2 (4.5) | 89.3 (2.6) | 88.6 (2.9) | — | 252.5 (92.3) |
| Relatively experienced | 9 | 81.0 (10.2) | 85.1 (8.7) | 84.4 (7.1) | — | 236.1 (51.9) |
| Beginners | 8 | 72.2 (14.3) | 76.3 (10.8) | 75.6 (8.2) | — | 206.6 (54.7) |
| Total | 23 | 79.6 (11.7) | 83.2 (9.8) | 82.4 (8.4) | — | 230.1 (65.0) |

SD: Standard Deviation
AUC: Area under the ROC curves

The sensitivity and the specificity of the Board Certified Gastroenterologists (n=6) among the 23 endoscopic examiners were 85.2% and 89.3%, respectively. The endoscopists had an extremely high sensitivity and specificity compared with the beginners group (n=8) the sensitivity of which was 72.2% and the specificity thereof was 76.3%. It should be noted that while the evaluation time of the Board Certified Gastroenterologists was 252.5±92.3 min that of the beginners group was 206.6±54.7 min. The sensitivity, the specificity, and the evaluation time by the relatively experienced group (n=9) each have middle values between those of the Board Certified Gastroenterologists and the beginners group.

[Performance of CNN]

The CNN constructed in the first embodiment provided an output of the probability P of *H. pylori* infection per image. This was followed by calculating standard deviation (SD) of samples per patient. Firstly, we examined characteristics of a primary CNN constructed by using all the training/validation data sets not having classified data included therein. FIG. 4 shows an ROC curve obtained from the examination. It should be noted that while the ROC curve originally has the abscissa representing "1-specificity", the left end serving as the origin "0", and the right end being "1", in FIG. 4 (similar in FIG. 5), the abscissa representing "specificity", the left end serving as the origin "1", and the right end being "0".

Each endoscopic examiner predicted *H. pylori* infection for each patient. White circles indicate the prediction results plotted for each endoscopic examiner. The black circle indicates the average predicted value for all the endoscopic examiners. The CNN outputs an *H. pylori* probability P per image and then the program calculates a standard deviation (SD) of the probabilities per patient.

In FIG. 4, the area under the ROC curve is 0.89, and at a cut-off value of 0.53 defined, the sensitivity and the specificity of the primary CNN were 81.9% and 83.4%, respectively. The time needed to diagnose all the images with the primary constructed CNN was 3.3 min. With this primary constructed CNN, 350 out of 397 patients were accurately diagnosed (88.2%). The average accuracy±SD by the endoscopic examiners for the cases of 47 patients misdiagnosed with the primary constructed CNN was 43.5±33.4%.

Next, an ROC curve of the secondary CNN constructed by using the same training/validation data set classified into a plurality of portions was obtained. FIG. 5 shows the resulting ROC curve. In FIG. 5, the CNN was structured through learning with the training/validation data set classified, only for a stomach, to a plurality of portions according to their location in the stomach, and the thus structured CNN outputs probabilities better than those with the primary CNN. The area under the ROC curve is 93%. White circles indicate the prediction results for each endoscopic examiner. The black circle indicates the average predicted value for all the endoscopic examiners. Both circles are plotted in the same manner as in FIG. 4.

In FIG. 5, the area under the ROC curve increased to 93% from 89% in FIG. 4. At the optimum cut-off value, which was 0.42, the sensitivity and the specificity of the CNN was 88.9% and 87.4%, respectively. These values were comparable to the diagnosis results from the Board Certified Gastroenterologists of the Japanese Gastroenterological Endoscopy Society, and were far higher than the beginners group. The time needed to diagnose all the images with a secondary CNN was 3.2 min.

From the foregoing, the diagnostic ability of the primary CNN is approximately middle between that of the beginners group and that the relatively experienced group, and the diagnostic ability of the secondary CNN is comparable to that of experienced endoscopists. Both of the primary and the secondary CNNs have the ability to diagnose in a dramatically shorter time compared with endoscopists. The result indicates that the *H. pylori* infection screening system with the CNN of the first embodiment has sensitivity and specificity sufficient enough to be applied to clinical practice.

Unlike the skin or retina, stomach is complex in its form, and gastroscopy images includes images that are acquired from different regions of the stomach, which have different appearances. Thus, use of CNN structured through learning by using the training/validation data sets not classified according to their location in the stomach makes it difficult to identify, in some cases, from what region the image was acquired. Thus, the use of the CNN structured with the training/validation data set classified, only for a stomach, to portions according to their location in the stomach increases the sensitivity from 81.9% to 88.9%, and increases the ability to diagnose *H. pylori*-infected gastritis.

It should be noted that endoscopic examiners and the CNN can be considered to recognize and diagnose images in different manners from each other. The gastric mucosal changes caused by *H. pylori* infection such as atrophy and intestinal metaplasia initially occur at the distal stomach (pylorus), and gradually expand to involve the proximal stomach (cardia). As such, in those stomachs having mild changes therein, the normal mucosa may be misdiagnosed as an abnormal mucosa. Endoscopists perform a diagnosis after identifying the location of the stomach in the image, in particular after recognizing the pylorus, the angle, the overall image, or the like.

In Japan, *H. pylori* infection is prevalent, especially among the elderly. The endoscopic mass screening for gastric cancer started in 2016 has resulted in necessitating a more efficient method of screening the images. The results obtained in the first embodiment suggest that connecting a large amount of stored images to this automated system largely helps screening of *H. pylori* infection even without evaluation of endoscopic examiners, and further testing can lead to confirmation of *H. pylori* infection, and finally result in eradication therapy.

The CNN of the first embodiment extremely shortens, without fatigue, the screening time for *H. pylori* infection, thus providing reports and results immediately after the endoscopic examination. Consequently, the CNN can contribute to reduction in burdening endoscopic examiners who perform *H. pylori* infection diagnosis and reduction in medical costs, which are important problems with global implications. Furthermore, the *H. pylori* diagnosis with the CNN of the first embodiment can promptly provide results when images obtained during endoscopic examination are input, thereby enabling the *H. pylori* diagnosis support to be done completely "online", and solving the problem of inadequate distribution of doctors in remote and distant locations through what is called "telemedicine".

While the secondary CNN of the first embodiment describes a case of learning with the training/validation data set classified into a plurality of portions according to their location, the number of the classified portions may be three to ten, which may be determined by the skilled person in the art as appropriate. It should be noted that in the construction of the secondary CNN, not only images of the stomach but also those of the pharynx, the esophagus, and the duodenum were included. To improve the diagnostic accuracy for *H. pylori*-positive or *H. pylori*-negative for a disease, the latter images were excluded.

Furthermore, the first embodiment describes a case of using training/trained images obtained by using the endoscope at regular magnification with white light. However, for a large number of images, it is also possible to use images obtained with an image-reinforcing endoscope or a magnifying endoscope and images obtained with Narrow Band Imaging (NBI, a method of observation by radiating laser beams having difference wavelengths. Refer to the above-described non-patent literature 3), an endoscope using stimulated Raman scattering microscopy (refer to the above-described patent literature 3), and the like.

The first embodiment uses both training/validation data set and test data set that were obtained at a single clinic alone. It is thought that adding examples in which images obtained at other facilities with other endoscope devices and techniques are used can make it possible to further improve the sensitivity and the specificity of the CNN. Furthermore, while in the first embodiment, patients who underwent *H. pylori* eradication were excluded, the CNN having learned images following *H. pylori* eradication becomes able to be used for determination whether *H. pylori* eradication is successful.

The status of *H. pylori* infection is confirmed with various tests such as blood or urine anti-*H. pylori* IgG levels measurement, fecal antigen tests, and urease breath test. In any of these tests, 100% sensitivity or 100% specificity cannot always be provided. Thus, the training/validation data set can contain an image that involves misdiagnosis. To solve this mixing of misdiagnosis, only images that are diagnosed as *H. pylori*-negative in a plurality of laboratory tests are increased, or images corresponding to classification such that diagnosis is made as *H. pylori*-negative in one test but *H. pylori*-positive in other tests, for example, are acquired and the CNN is trained by using training/validation data sets corresponding to the classification.

In the first embodiment, difference in the diagnostic ability was not evaluated according to the status of a stomach such as the degree of atrophy and the presence of diffuse redness. However, when the number of images for training is increased in future, the images for training are further classified according to such findings, so as to be memorized by the CNN. This can make it possible not only to determine whether *H. pylori*-infected gastritis occurs but also to perform determination on the findings equally to the Board Certified Gastroenterologists. In addition, in the first embodiment, endoscopic examination is described as support for diagnosis of *H. pylori* infection status of the stomach, the endoscopic examination is performed for not only the stomach but also the larynx, the pharynx, the esophagus, the duodenum, the bile duct, the pancreatic duct, the small intestine, the colon, and the like. When images for these regions are increasingly acquired and the number of images for training is increased, the images for training can be available in diagnosis support for these regions.

In particular, when a disease is colitis ulcerosa, extraction of features and analysis algorithm are similar to those in the case of determining the presence or absence of *H. pylori*-infected gastritis. Consequently, training a CNN using colon fiberscope images allows the CNN to easily output a result after being segmented in a plurality of stages according to the severity of the colitis ulcerosa. The colon fiberscope images that are training/validation data are classified into a plurality of portions according to their location in the colon in the same manner as in a stomach, and have definitive diagnosis results corresponding to being positive or negative for a disease of a disease of colitis ulcerosa and severity stages added thereto. By using the CNN trained based on the training/validation data composed of the colon fiberscope images and the definitive diagnosis results, it is possible to perform automated diagnosis for being positive or negative for a disease of the disease and the severity level on the test data composed of a plurality of colon fiberscope images for many subjects to be evaluated.

Because a process of creating data for training endoscopic images includes human manual operation, there can be an error in some pieces of data in training data. Mixing of the training data error has an adverse effect on determination accuracy of the CNN. Because endoscopic images used in the first embodiment are processed to have anonymity, it is impossible to confirm whether the training data has an error. To prevent an error from being contained in the training data as much as possible, images are mechanically classified based on the results of laboratory tests, so as to create training data sets with high quality. The CNN having learned with this training data can further improve the determination accuracy thereof.

It should be noted that while the first embodiment describes a case in which GoogLeNet is used as a CNN architecture, the CNN architecture has been developing on a daily basis, and employing the latest CNN architecture can give more favorable results. While Caffe, which is also an open source, was used as a deep learning framework, other frameworks such as CNTK, TensorFlow, Theano, Torch, and MXNet are usable. Furthermore, while Adam was used as an optimization method, other well-known methods such as Stochastic Gradient Descent (SGD), a MomentumSGV method having Momentum added to SGD, an AdaGrad method, an AdaDelta method, a NesterovAG method, and an RMSpropGraves method are selectable and usable as appropriate.

As in the foregoing, the diagnostic accuracy of *H. pylori* infection employing endoscopic images of a stomach with the CNN of the first embodiment was comparable to that of endoscopic examiners. Therefore, the CNN of the first embodiment is beneficial to selecting *H. pylori*-infected patients from obtained endoscopic images for various reasons such as screening. Furthermore, the CNN having learned images following *H. pylori* eradication can be used for determination whether *H. pylori* is eradicated. Whether *H. pylori* is eradicated is easily known by interview, and thus the *pylori* infection diagnosis has usability that allows immediate applicability in clinical site with this *H. pylori*-negative of a disease determination alone.

[Diagnosis Support System]

A computer having the CNN of the first embodiment, which serves as a diagnosis support system, embedded thereto basically includes an endoscopic image input unit, a storage unit (hard disk or semiconductor memory), an image analyzer, a determination display device, and a determination output device. The computer may additionally include a direct endoscopic image imaging device. A computer system including the computer having the system embedded therein can be installed away from an endoscopic examination facility, so as to receive image information from a remote site and serve as a central diagnosis support system, and also serve as a cloud computer system via the Internet.

This computer includes a first storage area that stores therein a plurality of endoscopic images of digestive organs, which are obtained in advance for a plurality of corresponding subjects, a second storage area that stores therein definitive diagnosis results of being positive or negative for the disease, which are obtained in advance for the corresponding subjects, and a third storage area that stores therein a CNN program. In this case, the number of the endoscopic images of a plurality of digestive organs, which are obtained in advance for the corresponding subjects, is large and the amount of data thereof is large, and the large amount of data is processed during the operation of the CNN program, and thus the computer favorably performs parallel processing and the storage unit thereof favorably has a mass storage.

Recently, CPU and GPU have remarkably developed in their performances. Computers having a CNN embedded therein, the CNN serving as a diagnosis support system used in the first embodiment, can process 3,000 or more cases per hour as an *H. pylori*-infected gastritis diagnostic system, when the computers are commercial personal computers having high efficiency to some extent. Such computers can process one image per approximately 0.2 second. Thus, providing image data that is being captured with an endoscope to the computers having the CNN used in the first embodiment embedded therein makes it possible to perform *H. pylori* infection determination real-time, and to remotely diagnose gastroscopic images transmitted from worldwide and remote places even if the images are moving images. In particular, computers in these years have been provided with GPU having excellent performance, so as to be able to perform fast image processing with high accuracy by having the CNN of the first embodiment being embedded therein.

Endoscopic images of digestive organs of subjects to be input to the input unit of the computer having a CNN being embedded therein, the CNN serving as the diagnosis support system of the first embodiment, may be images that are being captured with an endoscope, images transmitted via a communication network, or images recorded in a computer-readable recording medium. Specifically, the computer having embedded therein the CNN of the first embodiment, which serves as the diagnosis support system, can output, in a short time, respective probabilities of being positive and being negative for a disease of a digestive organ with respect to the endoscopic images of the digestive organ of the subjects that were input, so that the endoscopic images of the digestive organ of the subjects can be used regardless of the input format thereof.

It should be noted that, communication networks available include the well-known Internet, intranet, extranet, LAN, ISDN, VAN, CATV communication networks, virtual private network, telephone networks, mobile communication networks, and satellite communication networks. Furthermore, transmission media available in configuring communication networks include well-known IEEE1394 serial buses, USB, power line carriers, cable TV lines, telephone line circuits, wire transmission such as ADSL circuits, infrared rays, Bluetooth (trademark), wireless transmission such as IEEE802.11, mobile phone networks, satellite circuit, and radio transmission such as ground wave digital networks. Computer-readable recording medium available include well-known tapes such as magnetic tapes and cassette tapes, disc-based media including magnetic discs such as floppy disk (trademark) and hard disk, and optical discs such as compact disc-ROM/MO/MD/digital video disc/compact disc-R, card-based media such as IC cards, memory cards, and optical cards, and semiconductor memory such as mask ROM/EPROM/EEPROM/flash ROM.

Second Embodiment

The *H. pylori*-infected gastritis diagnostic system that includes the computer having embedded therein the CNN of the first embodiment, can automatically determine at what region an input image was captured. Thus, for classified seven regions, that is, cardia, gastric fundus, gastric corpus, angular region, antral zone, and antrum, this *H. pylori*-infected gastritis diagnostic system can display their respective *H. pylori* infection probabilities, and can display five regions with the highest five *H. pylori* infection probabilities, for example, out of the seven regions. Displaying *H. pylori* infection probabilities with corresponding classified regions eventually requires definitive diagnosis with blood and urine tests, and is useful for determination with endoscopists.

Figure 6:
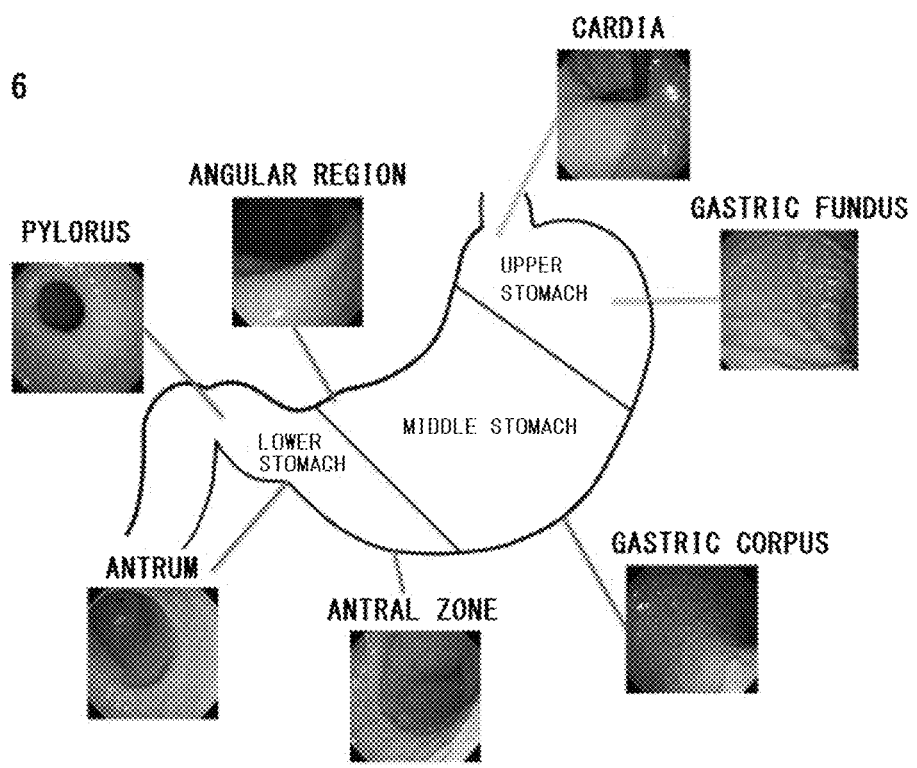
FIG. 6 is a diagram illustrating a major anatomical classification and quasi-anatomical classification for a stomach based on the guideline in Japan.

In the second embodiment, validation was performed that at what region an image was captured can be automatically determined. First, among EGD images obtained in the first embodiment, images that are unclear due to cancer, ulcer, residue/foreign object, bleeding, halation, partial blurring, or partial defocusing were excluded by the endoscopists, and remaining 27,335 images from 1750 patients were classified into six major categories (larynx, esophagus, duodenum, upper stomach, middle stomach, and lower stomach). Each of the major categories of a stomach includes, as shown in FIG. 6, a plurality of subcategories. The lower stomach includes pylorus, antrum, and antral zone, and the upper stomach includes cardia and gastric fundus, and the middle stomach includes angular region and gastric corpus.

These original 27,335 endoscopic images were randomly rotated from 0 degree to 359 degree with a tool in the same manner as in the first embodiment so that the images can be increased in number, and black frames surrounding respective images were automatically cropped, the images were enlarged or reduced as appropriate, only regular white-light images with regular magnification were included, enhanced images such as narrow band images were excluded, and training image data in excess of 1 million was obtained. The thus obtained training image data of the second embodiment is resized such that each image has 244×244 pixels so as to be compatible with GoogLeNet. The CNN system used in the second embodiment was trained by using the same training image data as for the CNN system of the first embodiment except that a learning rate was changed to 0.0002.

The trained CNN system of the second embodiment created a probability score (PS) for each image ranging from 0 to 100%. The PS shows the probability for a given image belonging to each of the anatomical classifications. The category with the highest PS was adopted as the final classification for the CNN, and the CNN-classified images were then evaluated manually by two endoscopists, so as to access whether they had been correctly classified. If the diagnosis differed between the two endoscopists, discussion was made to arrive at a satisfactory resolution.

Moreover, in order to evaluate the diagnostic accuracy of the CNN system, an independent set of 17,081 images from 435 patients receiving endoscopic examination at a clinic to which one of the inventors belongs between February 2017 and March 2017 were collected and prepared as a validation image set. The validation image set included only regular white light images with regular magnification. Enhanced images or images in which the anatomical classification could not be recognized were excluded from the validation image data in the same manner as for the training image data. Finally, the validation image data featured 17,081 images including 363 larynx images, 2,142 esophageal images, 13,047 stomach images, and 1,528 duodenum images (refer to Table 4).

TABLE 4

| Major classification | Sub-classification | Trained images (%) | Validation cases (%) |
|---|---|---|---|
| Pharynx | | 663 (2) | 363 (2) |
| Esophagus | Upper and middle | 1,460 (5) | 2,142 (13) |
| | Bottom | 1,792 (7) | |
| Upper stomach | Cardia | 1,830 (7) | 3,532 (21) |
| | Gastric fundus | 3,649 (13) | |
| Middle stomach | Angular region | 2,247 (8) | 6,378 (37) |
| | Gastric corpus | 4,937 (18) | |
| Lower stomach | Antrum | 2,517 (9) | 3,137 (18) |
| | Pylorus | 3,012 (11) | |
| | Antral zone | 2,010 (7) | |
| Duodenum | Bulb | 1,578 (6) | 1,528 (9) |
| | Descending part | 1,640 (6) | |
| Total | | 27,335 (100) | 17,081 (100) |

Figure 7:
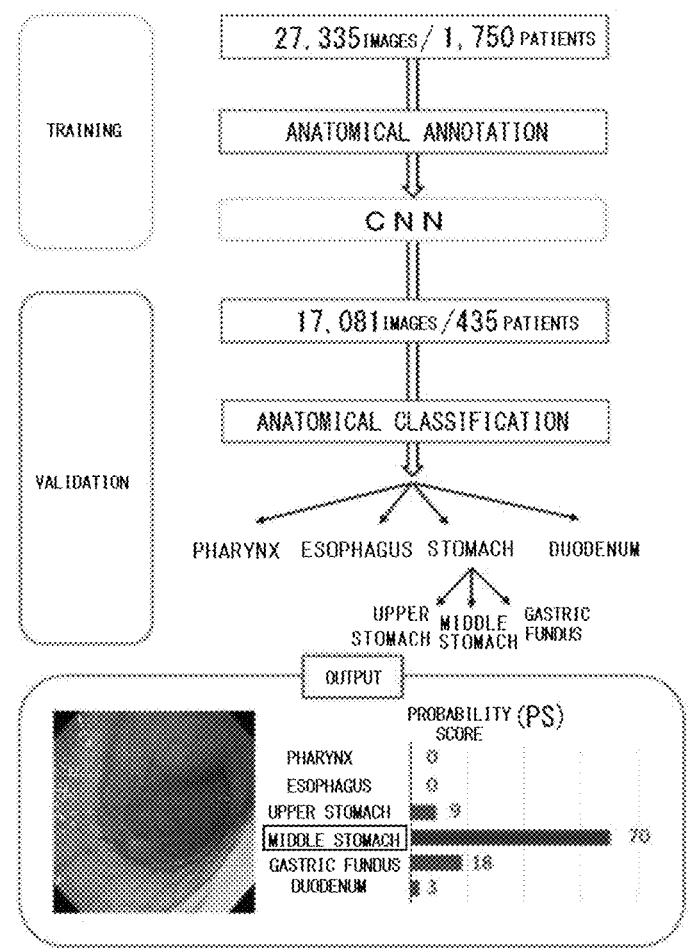
FIG. 7 is a schematic diagram illustrating a flowchart of a convolutional neural network (CNN) system according to a second embodiment.
Figures 8A, 8B, 8C, 8D:
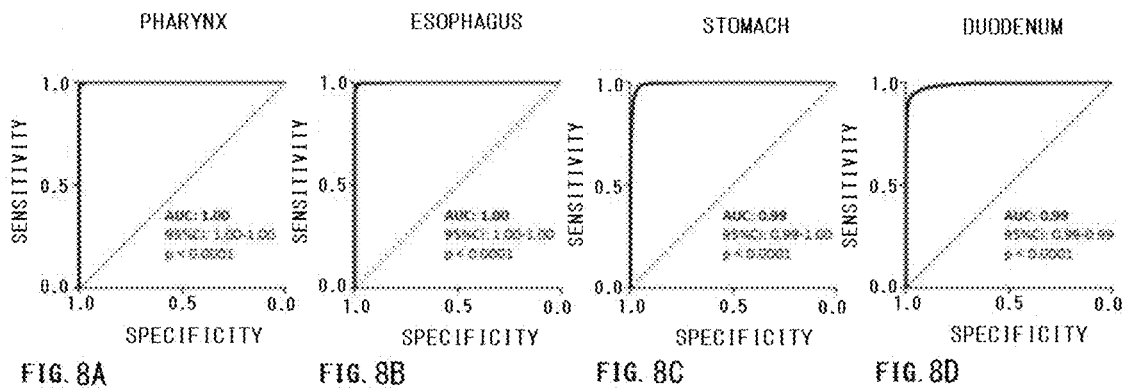
FIG. 8A is a diagram illustrating an ROC curve for a larynx image with a CNN system according to the second embodiment.
FIG. 8B is a diagram illustrating an ROC curve for an esophagus image according to the second embodiment.
FIG. 8C is a diagram illustrating an ROC curve for a stomach image according to the second embodiment.
FIG. 8D is a diagram illustrating an ROC curve for a duodenum image according to the second embodiment.

First, we evaluated whether the CNN system of the second embodiment was able to recognize images for the larynx, the esophagus, the stomach, and the duodenum. Next, as shown in FIG. 6, we evaluated whether the CNN system thereof was able to recognize the stomach location (upper stomach, middle stomach, lower stomach) based on the Japanese Classification of Gastric Carcinoma. Then, sensitivity and specificity were calculated for the anatomical classifications by the CNN system of the second embodiment. For the classification of each organ, receiver operating characteristic (ROC) curves were plotted, and the area under the curves (AUC) was calculated by GraphPad Prism 7 (GraphPad software, Inc., California, U.S.A.). FIG. 7 shows a brief summary of these study design.

First, GIE images were classified into four main categories (larynx, esophagus, stomach, and duodenum). The CNN system of the second embodiment accurately classified the anatomical location for 16,632 (97%) out of 17,081 images. The PS that the CNN system calculated ranged from 0 to 100%, and the individual highest PSs of 96% of the images were 90% or higher (refer to Table 5).

TABLE 5

| Probability score (PS) | Normal classification (%) | Total (%) | Accuracy (%) |
| --- | --- | --- | --- |
| >99% | 15,168 (91) | 15,265 (89) | 99.4 |
| 99-90% | 980 (6) | 1,101 (6) | 89.0 |
| 90-70% | 336 (2) | 437 (3) | 76.5 |
| 70-50% | 143 (1) | 264 (2) | 54.2 |
| <50% | 5 (0) | 14 (0) | 35.7 |
| Total | 16,632 (100) | 17,081 (100) | 97.4 |

Specifically, the CNN system of the second embodiment automatically recognized the anatomical location of the GIE images with AUC values of 1.00 [1.00[95% confidence interval (CI): 1.00 to 1.00, p<0.0001] for a pharynx, 1.00 (95% CI: 1.00 to 1.00, p<0.0001) for an esophagus, 0.99 (95% CI: 0.99 to 1.00, p<0.0001) for a stomach, and 0.99 (95% CI: 0.99 to 0.99, p<0.0001) for a duodenum (refer to FIG. 8A to FIG. 8D). It should be noted that the sensitivity and the specificity of the CNN system of the second embodiment for recognizing the anatomical location of each category were 93.9% and 100% for a larynx; 95.8% and 99.7% for an esophagus; 89.9% and 93.0% for a stomach; and 87.0% and 99.2% for a duodenum (refer to Table 6).

TABLE 6

| Output | Pharynx (n = 363) (%) | Esophagus ((n = 2,142) (%) | Stomach (n = 13,048) (%) | Duodenum (n = 1,528) (%) |
| --- | --- | --- | --- | --- |
| Pharynx | 341 (94) | 3 (0) | 1 (0) | 0 (0) |
| Esophagus | 5 (1) | 2,053 (96) | 28 (0) | 9 (0) |
| Stomach | 17 (5) | 75 (4) | 12,908 (99) | 189 (12) |
| Duodenum | 0 (0) | 11 (1) | 111 (1) | 1,330 (87) |
| Sensitivity (%) | 93.9 | 95.8 | 89.9 | 87.0 |
| Specificity (%) | 100 | 99.7 | 93.0 | 99.2 |

Next, we examined whether the CNN system of the second embodiment was able to correctly classify the anatomical location of image data obtained from different parts of a stomach. It is important to correctly classify the anatomical location in the stomach because some gastric diseases tend to occur in specific areas of the stomach. Training the CNN system of the second embodiment used a total of 13,048 stomach images, including 3,532 images from the upper stomach, 6,379 images from the middle stomach, and 3,137 images from the lower stomach.

Figures 9A, 9B, 9C:
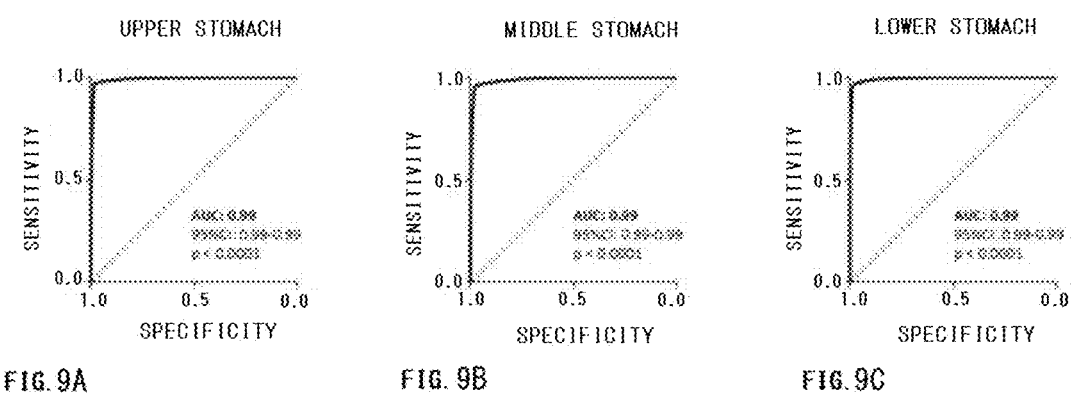
FIG. 9A is a diagram illustrating an ROC curve for an upper stomach according to the second embodiment.
FIG. 9B is a diagram illustrating an ROC curve for a middle stomach according to the second embodiment.
FIG. 9C is a diagram illustrating an ROC curve for a lower stomach according to the second embodiment.

The CNN system of the second embodiment accurately recognized the anatomical location of these stomach images with AUC values of 0.99 (95% CI: 0.99 to 0.99, p<0.0001) for the upper stomach, the middle stomach, and the lower stomach, as shown in FIG. 9. The sensitivity and the specificity of the CNN in classifying the anatomical location of each region were: 96.9% and 98.5% for the upper stomach, 95.9% and 98.0% for the middle stomach, and 96.0% and 98.8% for the lower stomach (refer to Table 7). Specifically, the CNN system of the second embodiment correctly classified the GIE image data into three anatomical locations in the stomach (upper stomach, middle stomach, and lower stomach).

TABLE 7

| Output | Upper stomach (n = 3,532) (%) | Middle stomach (n = 6,379) (%) | Lower stomach (n = 3,173) (%) |
| --- | --- | --- | --- |
| Upper stomach | 3,423 (97) | 148 (2) | 15 (0) |
| Middle stomach | 60 (2) | 6,119 (96) | 75 (2) |
| Lower stomach | 8 (0) | 32 (1) | 3,012 (96) |
| Other | 41 (1) | 80 (1) | 35 (1) |
| Sensitivity (%) | 96.9 | 95.9 | 96.0 |
| Specificity (%) | 98.5 | 98.0 | 98.8 |

[Evaluation of Images that were Incorrectly Classified]

Figures 10A, 10B:
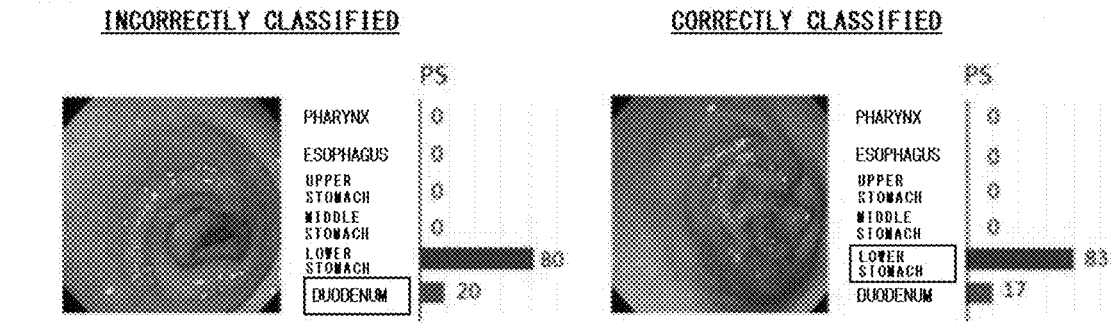
FIG. 10A is a diagram illustrating an image of a duodenum, in which the image is incorrectly classified as a lower stomach.
FIG. 10B is a diagram illustrating an image of a lower stomach, in which the image is correctly classified.

Finally, we reviewed images that had been incorrectly classified by the CNN in order to provide a basis for improving the performance of the CNN. FIG. 10 to FIG. 13 show typical examples of incorrectly classified images. FIG. 10A shows an image of the duodenum that was miss-classified as the lower stomach. FIG. 10B shows an image of the lower stomach that was correctly classified. As seen in these images, in landscape view, the duodenum sometimes shows a resemblance to the lower stomach; we believe that this was the cause of the incorrect classification.

Figure 11A:
FIG. 11A is a diagram illustrating an image of an esophagus, in which the image is incorrectly classified as a lower stomach.
Figure 11B:
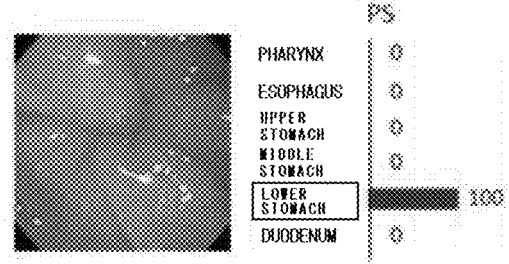
FIG. 11B is a diagram illustrating an image of a lower stomach that is correctly classified as a lower stomach.
Figure 12A:
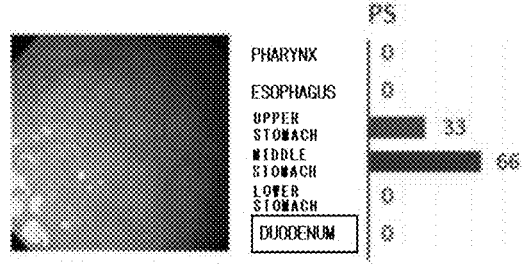
FIG. 12A is a diagram illustrating an image of a duodenum, in which the image is incorrectly classified as a lower stomach.
Figure 12B:
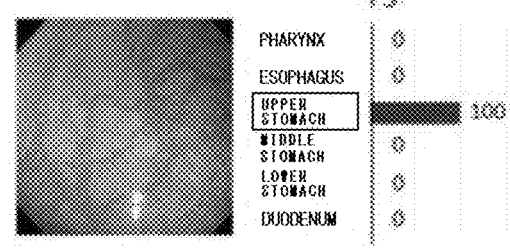
FIG. 12B is a diagram illustrating an image of an upper stomach, in which the image is correctly classified.
Figure 13A:
FIG. 13A is a diagram illustrating an image of a pharynx, in which the image is incorrectly classified as an esophagus.
Figure 13B:
FIG. 13B is a diagram illustrating an image of an esophagus that is correctly classified.

FIG. 11A shows an image of the esophagus that was incorrectly classified as the lower stomach. FIG. 11B shows an image of the lower stomach that was correctly classified as the lower stomach. FIG. 12A shows an image of the duodenum that was incorrectly classified as the middle stomach. FIG. 12B shows an image of the upper stomach that was correctly classified. FIG. 13A shows an image of the pharynx incorrectly classified as the esophagus. FIG. 13B shows an image of the esophagus that was correctly classified.

FIG. 11A and FIG. 12A show images in which gross structure could not be used for recognition due to insufficient insufflation of the lumen and/or the proximity of the scope to the luminal wall. In contrast, FIG. 13A shows an image of the larynx that was apparently different in its gross appearance, and was incorrectly classified as the esophagus.

Architecture for the classification of images is constantly advancing. Using such technology, the classification error rate was reported 3.0% to 7.3%, according to the latest results of the Imagenet Large Scale Visual Recognition Challenge 2016 (ILSVRC2016, http://image-net.org/challenges/LSVRC/2016/results). In contrast, the CNN system of the second embodiment showed a highly accurate classification results with high AUCs of 0.99 to 1.00, thus demonstrating the significant potential of CNN in the classification of GIE images according to anatomical location. This ability to recognize anatomical classification was an important step in clarifying whether CNN systems can be used in the diagnosis of gastrointestinal diseases by detecting lesions or abnormal findings automatically on images acquired from patients.

Because physicians need significant training, over several years, to become specialists of GIE, this CNN system can help to reduce their burden and also be beneficial for patients. In this regard, the results of the present invention show promising potential for the CNN system to establish a novel GIE support system. Furthermore, GIE images classification can itself be beneficial in the clinical setting because GIE images, which are automatically collected and stored electronically, are often reviewed by a second observer in order not to miss diseases; anatomically classified images are easier for the second observer to interpret and will thus reduce their burden.

Third Embodiment

A third embodiment describes a case in which a disease diagnosis support method employing endoscopic images, diagnosis support system, diagnosis a support program and a computer-readable recording medium having the diagnosis support program stored therein, which are of the present invention, are applied to the case of colitis ulcerosa. A retrospective review was performed for the patients' clinical data who underwent colonoscopy at a clinic to which one of the inventors belongs. Symptoms, endoscopic findings, and pathological findings of total 958 cases of patients are included. All of the patients underwent total colonoscopy and acquired colon fiberscope images were reviewed by three specialists of gastroenterology.

Figure 14A:
FIG. 14 is a diagram illustrating a typical colon fiberscope image that is classified into Mayo 0 to Mayo 3.
Figure 14B:
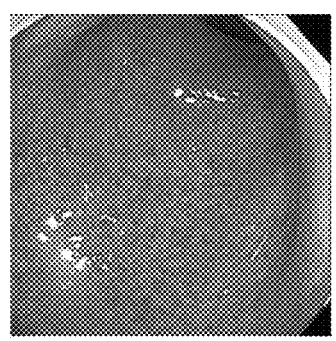
Figure 14C:
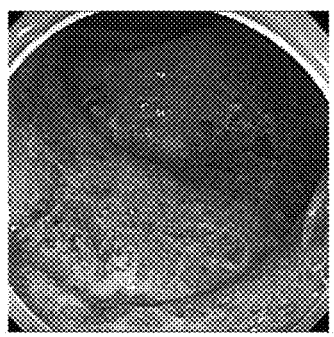
Figure 14D:
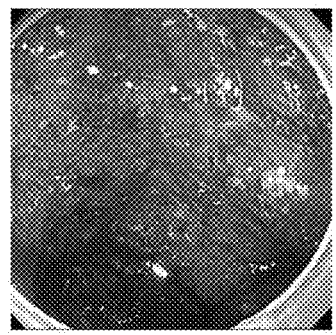

In the Third embodiment, only regular white-light images with regular magnification were included, enhanced images such as narrow band images were excluded. Unclear images with stool, blur, halation, or insufflation were also excluded, and the other clear images were classified by the locations of the colorectum, specifically, right colon (cecum, ascending and transverse colon), left colon (descending and sigmoid colon) and rectum, and also by each endoscopic disease activity according to the three Mayo endoscopic scores (Mayo 0, Mayo 1, and Mayo 2-3). FIG. 14 shows colon fiberscope images classified to typical rectum Mayo 0 to Mayo 3. It should be noted that FIG. 14A shows an example of Mayo 0, FIG. 14B shows an example of Mayo 1, FIG. 14C shows an example of Mayo 2, and FIG. 14D shows an example of Mayo 3.

When each of the reviewed images has different classifications with the reviewers, each image was reviewed by at least two of the three specialists of gastroenterology above and the Mayo endoscopic score was re-assigned for each image. The thus re-assigned Mayo endoscopic score is called "true-Mayo classification".

Total 26,304 images from 841 patients of colitis ulcerosa that were taken between October, 2006 to March, 2017 were used as a training data set, and 4,589 images from 117 patients of colitis ulcerosa that were collected between April to June, 2017 were used as a validation data set. Table 8 shows details of the patient characteristics of training data set and validation data set.

TABLE 8

| Mayo score | Region | Training data set (n) (%) | Validation data set (n) (%) |
| --- | --- | --- | --- |
| 0-1 | C-T (right colon) | 10,549 (40) | 1,882 (41) |
|  | D, S (left colon) | 6,720 (26) | 1,480 (32) |
|  | Rectum | 4,451 (17) | 821 (18) |

TABLE 8-continued

| Mayo score | Region | Training data set (n) (%) | Validation data set (n) (%) |
| --- | --- | --- | --- |
| 2-3 | C-T (right colon) | 539 (2) | 33 (1) |
|  | D, S (left colon) | 1,342 (5) | 105 (2) |
|  | Rectum | 2,703 (10) | 268 (6) |
| Total |  | 26,304 (100) | 4,589 (100) |

C-T: cecum, ascending and transverse colon
D, S: descending and sigmoid colon

These original endoscopic images were randomly rotated between 0 and 359 degrees, the black frame surrounding each image was cropped on each side and software was used to either zoom in or out by a factor of 0.9 or 1.1. Finally, the number of training images was amplified to in excess of 1 million.

All of the images were taken using standard colon fiberscope (EVIS LUCERA ELITE, Olympus Medical Systems, Co., Ltd., Tokyo, Japan).

All accompanying patient information was annotated prior to data analysis, and none of the endoscopists involved in the study were able to access any identifiable patient information. This study was approved by the Institutional Review Board of Japan Medical Association (ID: JMA-IIA00283). Informed consent was opted out because of the retrospective nature of this study using completely anonymized data.

The thus obtained training image data of the third embodiment is resized such that each image has 244×244 pixels so as to be compatible with GoogLeNet. The CNN system used in the third embodiment was trained by using the same training image data as for the CNN system of the first embodiment except that a learning rate was changed to 0.0002.

Figure 15:
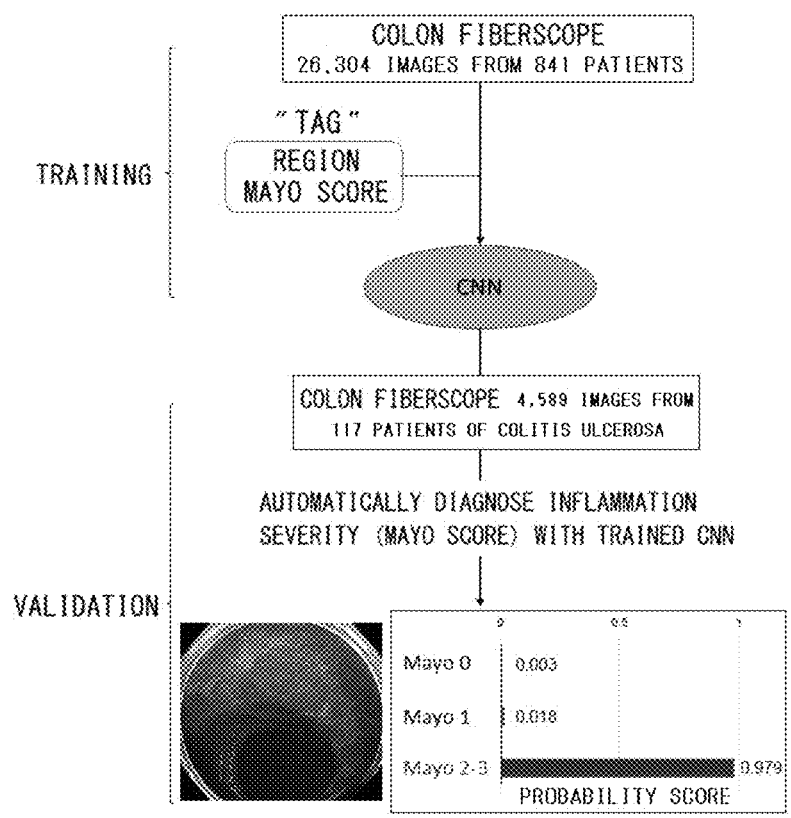
FIG. 15 is a schematic diagram illustrating a CNN-based diagnostic system according to a third embodiment.
Figure 16A:
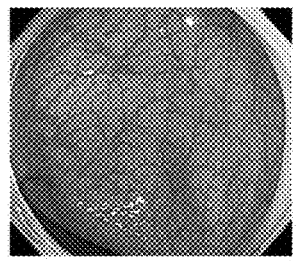
FIG. 16 is a diagram illustrating a typical image of the CNN of the third embodiment and an example of three Mayo classifications.
Figure 16A:
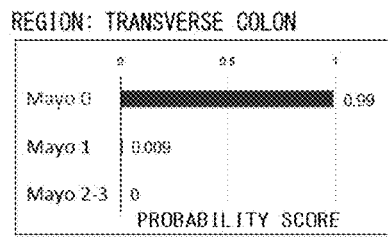
Figure 16B:
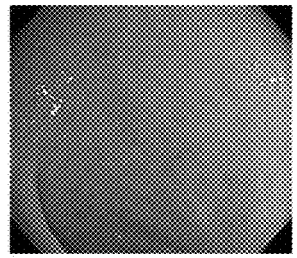
Figure 16B:
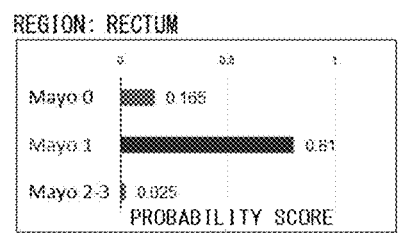
Figure 16C:
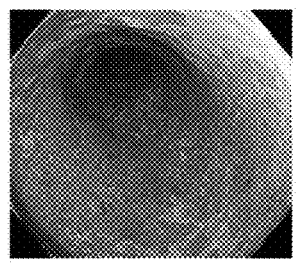
Figure 16C:
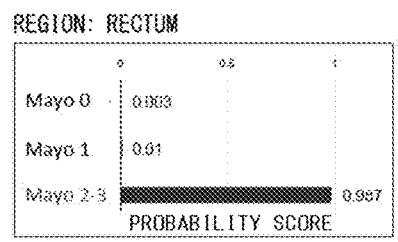

The trained CNN-based diagnostic system creates a probability score (PS) for each image ranging from 0 to 1, and the probability score indicates a probability that each image belongs to each Mayo endoscopic score. The category with the highest PS was adopted as the final classification for the CNN. FIG. 15 shows a brief summary of the CNN-based diagnostic system of the third embodiment. FIG. 16 shows typical images with the CNN of the third embodiment and an example of the obtained three Mayo endoscopic scores. It should be noted that, FIG. 16A is an example of the transverse colon classified to Mayo 0, FIG. 16B is an example of the rectum classified to Mayo 1, and FIG. 16C shows an example of the rectum classified to Mayo 2 or Mayo 3.

We validated the performance of the CNN by evaluating whether the CNN was able to classify each image into two classifications of Mayo 0-1 and 2-3. This is because Mayo 0 and Mayo 1 indicate a remission state (symptoms can be controlled) and Mayo 2 and Mayo 3 indicate the occurrence of inflammation. Receiver operating characteristic (ROC) curves were plotted for the classification of the Mayo endoscopic score, and the area under the ROC curves (AUC) with 95% confidence interval (CI) was calculated by Graph-Pad Prism 7 (GraphPad software, Inc., California, U.S.A.). Furthermore, AUC was evaluated in each location of the colorectum (right-sided colon, left-sided colon, and rectum).

Figure 17A:
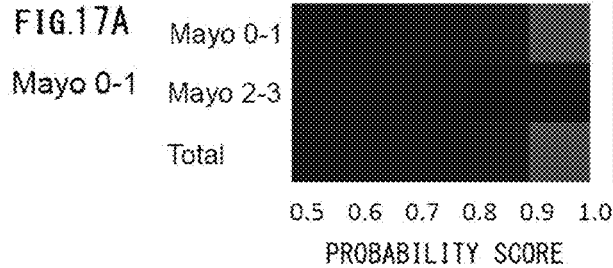
FIG. 17 is a diagram illustrating an ROC curve in two Mayo classifications according to the third embodiment.
Figure 17B:
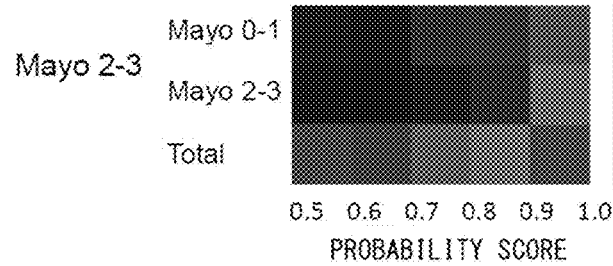

Table 9 shows association between true Mayo endoscopic scores and the two classifications of Mayo 0-1 and Mayo 2-3 by the CNN. FIG. 17A shows examples of probability scores with gray scales corresponding to the two Mayo endoscopic scores of Mayo 0-1 and Mayo 2-3. FIG. 17B shows an ROC curve for two Mayo endoscopic scores of Mayo 0-1 and Mayo 2-3.

TABLE 9

|  |  | True diagnosis results(n) (%) | |
|---|---|---|---|
|  |  | Mayo 0-1 | Mayo 2-3 |
| CNN diagnosis Results | Mayo 0-1 | 4,095 (96) | 208 (51) |
|  | Mayo 2-3 | 138 (4) | 198 (49) |
| Total |  | 4,183 (100) | 406 (100) |

Figure 17B:
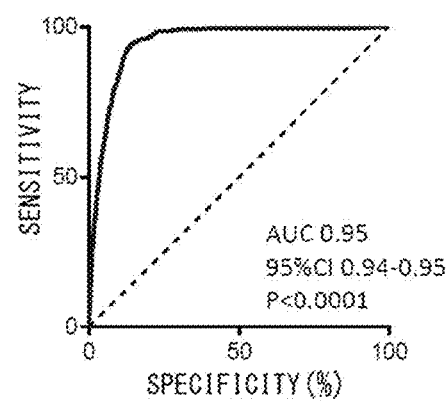

According to the results shown in Table 9 and FIG. 17, the CNN correctly classified 96% of Mayo 0-1 images and 49% of Mayo 2-3 images were correctly to respective Mayo endoscopic scores with the CNN. The ROC curve in FIG. 17B shows the high performance of the CNN with high AUC value of 0.95 (95% CI: 0.94-0.95) with respect to the two classifications of Mayo 0-1 and Mayo 2-3.

[The Association Between the True Mayo Classification and the CNN Classification by Each Location of Colorectum]

Because there was a possibility that the location of the colorectum affects the performance of the CNN, we evaluated the performance of the CNN by each location of colorectum (right sided colon, left sided colon, and rectum).

Table 10 shows the concordance between the AUC of the ROC curve, the true Mayo classification, and the CNN results in each location. The performances of the CNN were better in right-sided colon (AUC=0.96) and left-sided colon (AUC=0.97) than in rectum (AUC=0.88) in two classifications of Mayo 0-1 and Mayo 2-3.

TABLE 10

| | Mayo score 01-vs-2-3 | |
|---|---|---|
| Region | AUC (95% CI) | Concordance |
| C-T (right colon) | 0.96 (0.95-0.98) | 96% |
| D, S (left colon) | 0.97 (0.96-0.98) | 95% |
| Rectum | 0.88 (0.86-0.90) | 82% |

C-T: cecum, ascending and transverse colon
D, S: descending and sigmoid colon

As in the foregoing, we confirmed that, according to the third embodiment, the trained CNN was able to identify endoscopic disease activities in colitis ulcerosa images, and showed promising performance to differentiate images with severe inflammation (Mayo 2, Mayo 3) from images with a remission state (Mayo 0, Mayo 1).

According to the results of the third embodiment, the CNN showed extremely favorable performance in recognition of a mucosal healing state (Mayo 0, Mayo 1), with recognition in rectum being better than in right colon and left colon. One of the reasons for this is the images were mostly from colitis ulcerosa patients who were under treatment. The treatment modifies the inflammation severity and this leads the inflammation to "patchy" or "skip lesion", thereby making it difficult to classify the Mayo endoscopic score properly. This can lead to the lower performance of the CNN classification in the rectum, because rectum has several treatment options and patchiness or skip lesion often occurs.

Furthermore, in the third embodiment, we defined the CNN classification as the Mayo endoscopic score with the highest probability score. Therefore, even the images with PS of 0.344 (the lowest value) for Mayo 1 probability score was classified as Mayo 1 that is the same as that for the images with PS of 1.00 for Mayo 1. This is one of the reasons that the concordance between the true Mayo score and the CNN classification is relatively low compared to AUC values. Thus, by setting an optimal cut-off value for the PS to define the CNN classification, the performance of the CNN can be improved.

There are several limitations in the third embodiment. First, this is the retrospective study and the prospective study is necessary to evaluate the performance of the CNN in the real clinical settings. Second, because all of the colonoscopy images were collected in a family clinic that does not have an admission facility, the number of images with Mayo 2-3 was relatively small in both training and validation data sets. Therefore, training the CNN with much more Mayo 2-3 images may make the performance of the CNN better.

Fourth Embodiment

A fourth embodiment describes a case in which a disease diagnosis support method employing endoscopic images, a diagnosis support system, a diagnosis support program and a computer-readable recording medium having the diagnosis support program stored therein, which are of the present invention, are applied to the case of an esophagus disease by using Endocytoscopy (ECS) system. The ECS system used in the fourth embodiment is a new magnifying endoscopic examination system that allows users to observe surface epithelial cells in vivo real-time by using vital stain such as methylene blue. The inventors performed clinical test with the ECS for the first time in 2003, and reported characteristics of normal squamous and characteristics of surface epithelial cells of esophageal cancer (refer to non-patent literature 4). The fourth generation ECS currently on the market has optically 500 magnifications, and can expand the magnifications to maximum 900 magnifications with a digital expansion function built in a video processor.

Between November 2011 and February 2018, at a clinic to which one of the inventors belongs, to 241 patients in the clinic, 308 cases of esophagus ECS examination were performed. For scopes, two types of prototype ECS (Olympus Medical Systems, Co., Ltd.) were used, specifically, GIF-Y0002 (optical magnification: 400 (digital magnification: 700)), and GIF-Y0074 (optical magnification: 500 (digital magnification: 900)). For endoscope video scope system, a standard endoscope video system (EVIS LUCERA CV-260/CLV-260, EVIS LUCERA ELITE CV-290/CLV-290SL: Olympus Medical Systems, Co., Ltd.) was used.

As shown in FIG. 18, endoscopic images with the maximum optical magnification of the ECS (low-magnification images, a to e in FIG. 18) and endoscopic images of 1.8 digital magnifications (high-magnification images, f to j in FIG. 18) were saved together. Among 308 cases of the ECS examination, 4,715 images from 240 cases between November 2011 and December 2016 were adopted for training data sets for the development of algorithm to analyze the ECS images.

Training data sets were constituted of 126 cases of esophageal cancer (58 cases of superficial cancer, 68 cases of progressive cancer), 106 cases of esophagitis (52 cases of radiation related esophagitis, 45 cases of gastro-esophagus reflux disease, candida esophagitis, two cases of eosinophilic esophagitis, three cases of esophagitis), and eight cases of normal squamous disease. All the lesions were histologically diagnosed by using biopsy tissues or resected specimens. Finally, the training data sets were classified into "malignant images (the number of images: 1,141 (low-magnification images: 231, high-magnification images: 910)), and "non-malignant images (the number of images: 3,574 (low-magnification images: 1,150, high-magnification images: 2,424))". In the fourth embodiment, the CNN was trained by using both of low-magnification images and high-magnification images.

Test data sets for the evaluation of the diagnostic ability of the constructed CNN used 55 cases in which the form of superficial cells of esophagus was able to be favorably observed with the ECS. The test data used 1,520 images (low-magnification images: 467 and high-magnification images: 1,053) constituted of 27 cases of malignant lesion and 28 cases of non-malignant lesion. All the cases of malignant lesion were esophagus squamous cancer. These 27 cases of malignant lesion are constituted of 20 cases of superficial cancer and seven cases of progressive cancer. The 28 cases of non-malignant lesion are constituted of 27 cases of esophagitis (14 cases of radiation related esophagitis, nine cases of gastro-esophagus reflux disease (GERD), and four cases of esophagitis) and one case of esophagus papilloma.

The thus obtained training image data of the third embodiment is resized such that each image has 244×244 pixels so as to be compatible with GoogLeNet. The CNN system used in the fourth embodiment was trained by using the same training image data as for the CNN system of the first embodiment.

[CNN Diagnosis Results]

We examined the test data after the construction of the CNN using the training data set. For each image of the test data, a probability of being malignant was calculated, receiver operating characteristic (ROC) curves were plotted, and the area under the ROC curves (AUC) were calculated. A cut-off value was determined considering the sensitivity and the specificity of the ROC curves.

In examination for each case, when at least two images out of a plurality of the ECS images obtained from the same lesion, the case was diagnosed as malignant. The sensitivity, a positive predictive value (PPV), a negative predictive value (NPV), and the specificity of the CNN that diagnoses esophageal cancer were calculated as follows:

Sensitivity=Number of images that the CNN correctively diagnosed as malignant/Number of histologically proven esophageal cancer lesions PPV=Number of images that the CNN correctly diagnosed as malignant/Number of lesions diagnosed by the CNN as esophageal cancer NPV=Number of images that the CNN correctly diagnosed as non-malignant lesion(no more than one ECS image was diagnosed as malignant)/Number of lesions diagnosed by the CNN as non-malignant lesion Specificity=Number of images that the CNN correctly diagnosed as non-malignant lesion/Histologically proven non-malignant lesion Prior to the CNN diagnosis, one experienced endoscopist performed diagnosis during endoscopic examination. The endoscopist classified all the cases based on the following type classification:

Type 1: Superficial cells have a low nucleo-cytoplasmic ratio and a low cell density. No dyskaryosis is recognized (refer to FIG. 19a).

Type 2: A nuclear density is high, but no apparent dyskaryosis is recognized. Boundary between cells is unclear. (Refer to FIG. 19b.)

Type 3: Apparent increase in a nuclear density and dyskaryosis are recognized. Nuclear swelling is also recognized. (Refer to FIG. 19c.)

[Clinical Diagnosis on Test Data and Pathological Findings]

Table 11 shows clinical diagnosis of test data cases and pathological findings.

TABLE 11

| Clinical diagnosis | Pathological diagnosis | Number of cases |
| --- | --- | --- |
| Esophageal cancer | Squamous cancer | 27 |
| Gastro-esophagus reflux disease | Esophagitis | 2 |
|  | Esophagitis regenerated squamous | 4 |
|  | Esophagus ulcer | 3 |
| Radiation esophagitis | Esophagitis | 8 |
|  | Esophagitis regenerated squamous | 2 |
|  | Esophagus ulcer | 1 |
|  | Esophagitis due to idioblast | 1 |
|  | Granulation tissue | 1 |
|  | Necrotic tissue | 1 |
| Other esophagitis | Esophagitis | 4 |
| Papilloma | Papilloma | 1 |

As shown in Table 11, all the 27 cases diagnosed by the clinical diagnosis as esophageal cancer were squamous cancer. Among nine cases diagnosed by the clinical diagnosis as gastro-esophagus reflux disease, four cases were diagnosed as histologically regenerated epithelial, three cases as esophagus ulcer, and two cases as esophagitis. Among 14 cases diagnosed by the clinical diagnosis as radiation esophagitis, two cases were histologically diagnosed as regenerated epithelial, eight cases as esophagitis, and other cases as esophagus ulcer, esophagitis with atypical cells, granulation tissue and necrotic tissue.

[ROC Curve, Area Under the ROC Curve and the Cut-Off Value]

The CNN of the fourth embodiment requires 17 seconds to analyze 1,520 images (0.011 sec per image). The AUC calculated from the ROC curve plotted from all the images (FIG. 20A) was 0.85. The AUC calculated for an ROC curve plotted from high-magnification images (FIG. 20B) was 0.90, and the AUC for an ROC curve plotted from low-magnification images (FIG. 20C) was 0.72.

With expectation for high specificity to non-malignant lesion, a cut-off value of a probability of malignant tumor was set to 90% from the ROC curve. As shown in Table 12, for all the images, the sensitivity was 39.4, the specificity was 98.2, PPV was 92.9, and NPV was 73.2. When high-magnification images and low-magnification images are separately analyzed, for the high-magnification images, the sensitivity, the specificity, PPV, and NPV are respectively, 46.4, 98.4, 95.2, and 72.6, and for the low-magnification images, the sensitivity, the specificity, PPV, and NPV are respectively 17.4, 98.2, 79.3, and 74.4.

TABLE 12

|  | CNN sensitivity | Specificity | Positive predictive value (PPV) | Negative predictive value (NPV) |
| --- | --- | --- | --- | --- |
| All images | 39.4 | 98.2 | 92.9 | 73.2 |
| High-magnification image (HMP) | 46.4 | 98.4 | 95.2 | 72.6 |

TABLE 12-continued

| | CNN sensitivity | Specificity | Positive predictive value (PPV) | Negative predictive value (NPV) |
|---|---|---|---|---|
| Low-magnification image (LMP) | 17.4 | 98.2 | 79.3 | 74.4 |

Among 622 cases clinically diagnosed as non-malignant for high-magnification images, 10 images (1.6%) have probabilities of malignant tumor exceeding 90%. These 10 images included seven images obtained from a white spot part, two images obtained from atypical epithelia, and one image obtained from normal epithelia. Among 332 cases clinically diagnosed as non-malignant for low-magnification images, seven images (2.1%) diagnosed as esophagitis had probabilities of malignant exceeding 90%.

[Comparison Between Evaluation of Types Classified by the Endoscopist for Each Case and CNN Diagnosis]

Table 13 shows relations between diagnosis results with the CNN constructed in the fourth embodiment and types classified by the endoscopist, among 27 cases diagnosed as esophagus squamous cancer.

TABLE 13

| | CNN diagnosis | | Classification by endoscopist | | |
|---|---|---|---|---|---|
| | Malignant | Non-malignant | Type 3 | Type 2 | Type 1 |
| Malignant | 25 | 2 | 27 | 0 | 0 |
| Non-malignant | 3 | 25 | 3 | 12 | 13 |

According to the results shown in Table 13, among 27 cases diagnosed as esophagus squamous cancer, the CNN correctly diagnosed 25 cases (sensitivity 92.6%) as malignant (including at least two images with probabilities of malignant tumor exceeding 90%). The median (range) of percentage of pictures with cancer cells that the CNN recognized as malignant was 40.9 (0 to 88.9)%. The CNN correctly diagnosed 25 cases as non-malignant (specificity 89.3%) out of 28 cases of non-malignant lesion. The PPV, the NPV, and the overall accuracy were 89.3%, 92.6%, and 90.9%, respectively.

The endoscopist diagnosed all the malignant lesions as Type 3. The endoscopist diagnosed, out of 28 cases of non-malignant lesions, 13 lesions as Type 1 and 12 lesions as Type 2, and three lesions as Type 3. When it is considered that Type 3 corresponds to malignant tumor, the sensitivity, the specificity, the PPV, the NPV, and the endoscopic examination were 100%, 89.3%, 90.0%, 100%, and 94.5%, respectively, in the comprehensive accuracy of diagnosis.

Figure 21A:
FIG. 21A is a diagram illustrating a regular endoscopic image.
Figure 21B:
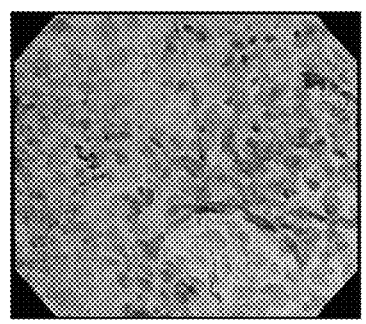
FIG. 21B is a diagram illustrating an endocytoscopy image.
Figure 21C:
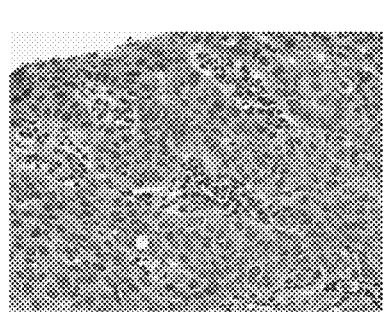
FIG. 21C is a diagram illustrating a histopathological examination image.

Two cases of malignant legion diagnosed by the CNN as non-malignant were correctly diagnosed by the endoscopist as Type 3. These two cases were of superficial cancer and apparently had increase in a nuclear density and abnormality in nucleus. However, nuclear swelling was not recognized (refer to FIG. 21). It should be noted that FIG. 21A shows a regular endoscopic image, FIG. 21B shows an ECS image, and FIG. 21C shows a histopathological examination image.

Figure 22A:
FIG. 22A is a diagram illustrating a regular endoscopic image.
Figure 22B:
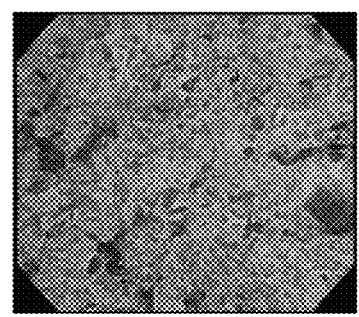
FIG. 22B is a diagram illustrating an endocytoscopy image.
Figure 22C:
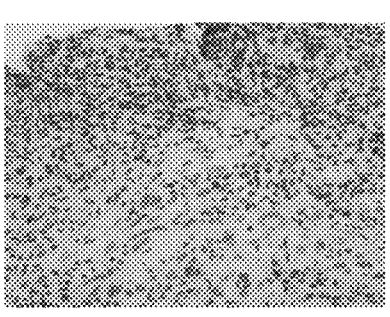
FIG. 22C is a diagram illustrating a histopathological examination image.

Among three cases in which the CNN diagnosed non-malignant legion as malignant, two cases were of esophagitis after radiation exposure, and one case was of gastro-esophagus reflux disease of Grade C. From the non-magnifying endoscopic images of these lesions, the endoscopist did not recognize the images as malignant. However, the endoscopist classified the case of the esophagitis after radiation exposure as Type 3 due to apparent increase in a nuclear density and nuclear abnormality therefor. The histological examination for the lesion part revealed that this case was of granulation tissue (refer to FIG. 22). It should be noted that, FIG. 22A shows a regular endoscopic image, FIG. 22B shows an ECS image, and FIG. 22C a histopathological examination image.

The most promising object of ECS diagnosis for esophagus is to omit biopsy tissue diagnosis for esophagus squamous cancer. According to the results of the fourth embodiment, the ROC curve for high-magnification images, in particular, showed high AUC. Previously, we tested whether one clinical pathologist was able to differentiate a malignant ECS image from ECS images alone. A pathologist diagnosed approximately two-thirds the esophagitis as malignant by using low-magnification images alone. In this case, it was possible to recognize increase in a nuclear density, but not possible to recognize dyskaryosis due to low magnification. After that, for recognition of dyskaryosis, we performed re-test with images of 1.8 digital magnifications (high-magnification). As a result, the pathologist dramatically improved in the sensitivity and the specificity by 90% or higher.

In the fourth embodiment, all the non-malignant low-magnification images diagnosed as malignant were obtained from esophagitis cases. While these images showed a high nuclear density, abnormality in nucleus therefor could not be evaluated due to low magnification. Therefore, it is recommendable to refer to high-magnification images instead of low-magnification images. In contrast, most of the non-malignant high-magnification images misdiagnosed as malignant were obtained based on observation on a white spot part. One of the characteristics of ECS images from the white spot part is aggregation of inflammatory cells. It is estimated that these ECS images were recognized as low-magnification images for squamous cancer (refer to FIG. 18). Thus, two different CNNs are desirably established in future for high-magnification images and low-magnification images, separately.

To omit tissue biopsy, minimizing misdiagnosis (false-positive), in which non-malignant legion is taken as malignant, is essential. Overdiagnosis on squamous tumor by the endoscopist using ECS leads to surgery with risk of death. In paper discussing application of AI for early detection of cancer, a certain false-positive rate is allowed. This cut-off value is set comparatively with low probability. In the present study, we set a cut-off value for the probability of malignant tumor to 90%. The reason for this is to minimize the above-described false-positive.

For evaluation for each case, the endoscopist adopted Type classification for diagnosis with ECS. Type 1 and Type 3 correspond to non-neoplastic epithelia and esophagus squamous cancer, respectively. In these cases, tissue biopsy can be omitted. However, because Type 2 includes various histological statuses, to decide the treatment policy, it is required to perform tissue biopsy. According to the results of the fourth embodiment, the diagnosis result by the CNN on the ECS images showed accuracy exceeding 90%, which is close to the result of the endoscopist.

This result is allowable despite the high cut-off value. With the support by the CNN, these cases can omit tissue biopsy. Furthermore, two malignant cases not diagnosed by the CNN as malignant were accurately diagnosed by the endoscopist as Type 3. These cases are apparently seen as malignant tumor through regular endoscopic observation for lesion, and thus the cases need only ECS images alone and can omit tissue biopsy without support by the CNN.

In contrast, the specificity in the fourth embodiment was 89.3% and three cases of non-malignant lesion were diagnosed by the CNN as malignant. One case was a gastroesophagus reflux disease of Grade C and the other two cases were radiation esophagitis. Pathological diagnoses of these legions were regenerated epithelial, granulation tissue, and esophagus ulcer. It is difficult even for experienced pathologists to differentiate regenerated epithelial from esophagus squamous cancer.

One case of radiation esophagitis was diagnosed by the endoscopist as Type 3 and by the CNN of the fourth embodiment as malignant. In some cases, it is difficult to diagnose recurrence or residual esophageal cancer even with tissue biopsy after radiation exposure. In addition to ECS observation, tissue biopsy is required to follow up esophageal cancer after radiation exposure.

According to the results of the fourth embodiment, in the present CNN study, some limitations can be pointed out. First, the number of pieces of test data was small. To solve this problem, acquiring a huge number of images from moving images is being projected. It is expected that CNN that has further deeply learned will improve in diagnosis results. Second, two different ECS systems having different optical magnifications of 400 and 500 were used. Difference in magnification between these two ECS systems can have an effect on the CNN diagnosis results. Thus, images will be required to be limited to those obtained by using commercially available ECS having optical magnification of 500.

In conclusion, the CNN of the fourth embodiment is able to strongly support endoscopists in omitting tissue biopsy based on ECS images. Furthermore, to recognize dyskaryosis it is required to refer to high-magnification images with digital zoom being used instead of low-magnification images.

Fifth Embodiment

Figure 23:
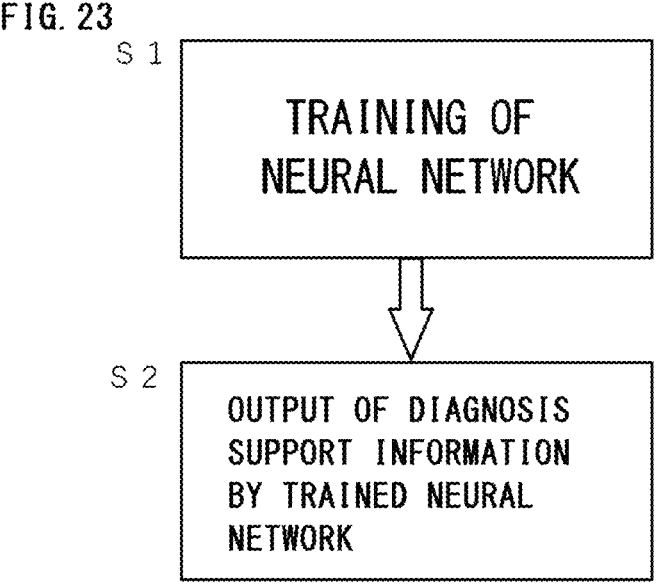
FIG. 23 is a block diagram illustrating the disease diagnosis support method employing endoscopic images of a digestive organ using a neural network according to a fifth embodiment.

With reference to FIG. 23, a disease diagnosis support method employing endoscopic images of a digestive organ using a neural network of a fifth embodiment is described. In the fifth embodiment, it is possible to use the disease diagnosis support method employing endoscopic images of a digestive organ using the neural network according to the first to the fourth embodiments. At S1, the neural network is trained by using first endoscopic images of a digestive organ, and corresponding to the first endoscopic images, at least one definitive diagnosis result of being positive or negative for the disease of the digestive organ, a past disease, a severity level, and information corresponding to an imaged region. At S2, the neural network trained at S1 outputs, based on second endoscopic images of the digestive organ, at least one of a probability of being positive and/or negative for the disease of the digestive organ, a probability of a past disease, a severity level of the disease, and the information corresponding to the imaged region.

At S1, the first endoscopic images may be adjusted in contrast. Furthermore, at S1, each of the first endoscopic images may be associated with the imaged region. The region may include at least one of a pharynx, an esophagus, a stomach, and a duodenum, and the region may be segmented in a plurality of portions for at least one of a plurality of digestive organs. When the region is a stomach, the segment can include at least one of an upper stomach, a middle stomach, and a lower stomach. The segment can include at least one of a cardia, a gastric fundus, a gastric corpus, an angular region, an antral zone, an antrum, and a pylorus.

when the number of the first endoscopic images in one of the imaged regions is smaller than that in another region, by using at least one of rotation, enlargement, reduction, change in the number of pixels, extraction of bright and dark portions, and extraction of portions having change in hue, for the first endoscopic images, the number of the first endoscopic images can be made substantially equal in every region.

The trained neural network may be capable of outputting information corresponding to a region at which the second endoscopic images have been imaged, and may output the probability and the severity level together with information corresponding to the region.

The first endoscopic images that include gastroscopic images may include at least one of with or without H. pylori infection and with or without H. pylori eradication. The first endoscopic images that include colon fiberscope images may include at least colitis ulcerosa as a disease, and the trained neural network may output a result after being segmented in a plurality of stages according to the severity level of the colitis ulcerosa. The first endoscopic images that include esophagus endoscopic images may include at least one of esophageal cancer, gastro-esophagus reflux disease, and esophagitis, as a disease, and the trained neural network may output a result after being segmented for at least one of esophageal cancer, gastro-esophagus reflux disease, and esophagitis.

The second endoscopic images may be at least one of images that are being captured with an endoscope, images transmitted via a communication network, images to be provided from a remote operation system or a cloud system, images stored in a computer-readable recording medium, and moving images. A convolutional neural network may be used as a neural network.

Sixth Embodiment

Figure 24:
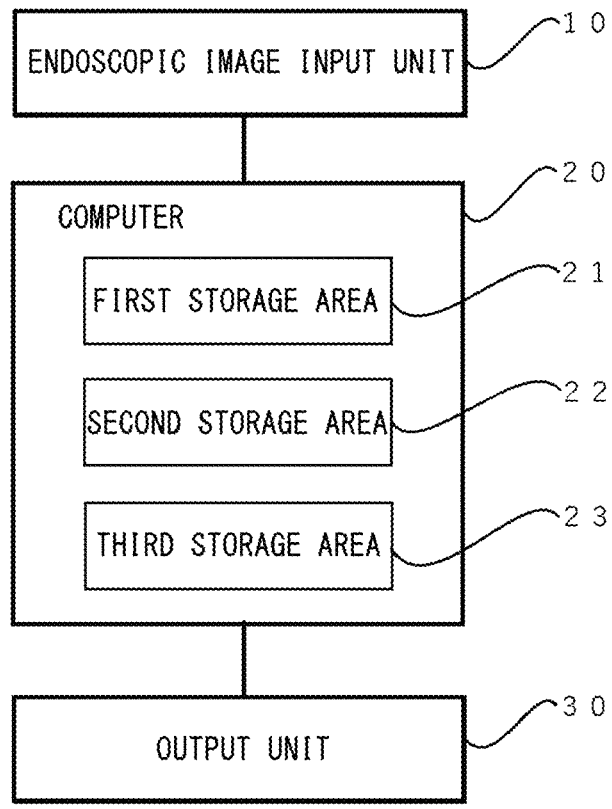
FIG. 24 is a block diagram illustrating a disease diagnosis support system employing endoscopic images of a digestive organ using a neural network according to a sixth embodiment, a diagnosis support program based on endoscopic images of a digestive organ, and a computer-readable recording medium.

With reference to FIG. 24, a disease diagnosis support system employing endoscopic images of a digestive organ using a neural network of a sixth embodiment, a diagnosis support program based on the endoscopic images of the digestive organ, and a computer-readable recording medium are described. In the sixth embodiment, it is possible to use the disease diagnosis support system employing endoscopic images of a digestive organ described in the first embodiment to the fourth embodiment. The disease diagnosis support system employing endoscopic images of a digestive organ includes an endoscopic image input unit 10, an output unit 30, and a computer 20 having the neural network embedded therein. The computer 20 includes a first storage area 21 that stores therein first endoscopic images of a digestive organ, a second storage area 22 that stores therein at least one definitive diagnosis result, corresponding to the first endoscopic images, of being positive or negative for the disease of the digestive organ, a past disease, a severity level, and information corresponding to an imaged region, and a third storage area 23 that stores therein the neural network program. The neural network program stored in the third storage area 23 is trained based on the first endoscopic images stored in the first storage area 21 and the definitive diagnosis result stored in the second storage area 22. The neural network program outputs, based on the second endoscopic images of the digestive organ input from the endoscopic image input unit 10, at least one of a probability of being positive and/or negative for the disease of the digestive organ with respect to the second endoscopic images, a probability of a past disease, a severity level of the disease, and information corresponding to the imaged region, to the output unit 30.

The first endoscopic images may be adjusted in contrast. Each of the first endoscopic images may be associated with the imaged region. The region may include at least one of a pharynx, an esophagus, a stomach, and a duodenum. The region may be segmented in a plurality of portions for at least one of a plurality of digestive organs. When the region is a stomach, the segment can include at least one of an upper stomach, a middle stomach, and a lower stomach. The segment can include at least one of a cardia, a gastric fundus, a gastric corpus, an angular region, an antral zone, an antrum, and a pylorus.

when the number of the first endoscopic images in one of the imaged regions is smaller than that in another region, by using at least one of rotation, enlargement, reduction, change in the number of pixels, extraction of bright and dark portions, and extraction of portions having change in hue, for the first endoscopic images, the number of the first endoscopic images can be made substantially equal in every region.

The trained neural network may be capable of outputting information corresponding to a region at which the second endoscopic images have been imaged, and may output the probability and the severity level together with information corresponding to the region.

The first endoscopic images that include gastroscopic images may include at least one of with or without *H. pylori* infection and with or without *H. pylori* eradication. The first endoscopic images that include colon fiberscope images may include at least colitis ulcerosa as a disease, and the trained neural network may output a result after being segmented in a plurality of stages according to the severity level of the colitis ulcerosa. The first endoscopic images that include esophagus endoscopic images may include at least one of esophageal cancer, gastro-esophagus reflux disease, esophagitis, as a disease, and the trained neural network may output a result after being segmented, for at least one of esophageal cancer, gastro-esophagus reflux disease, and esophagitis.

The second endoscopic images may be at least one of images that are being captured with an endoscope, images transmitted via a communication network, images to be provided from a remote operation system or a cloud system, images stored in a computer-readable recording medium, and moving images. A convolutional neural network may be used as a neural network.

The disease diagnosis support system employing endoscopic images of a digestive organ includes a diagnosis support program based on endoscopic images of a digestive organ as means for the computer to operate. The diagnosis support program based on endoscopic images of a digestive organ can be stored in a computer-readable recording medium.

Seventh Embodiment

Figure 25:
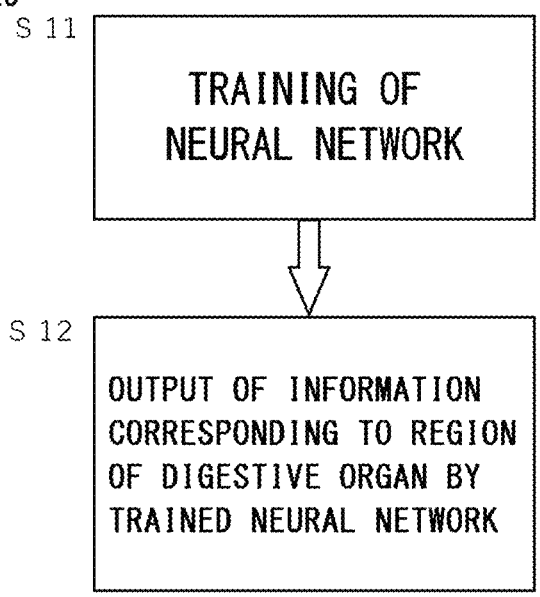
FIG. 25 is a block diagram illustrating a region determination method for a digestive organ employing endoscopic images of the digestive organ using a neural network according to a seventh embodiment.

With reference to FIG. 25, a region determination method for a digestive organ employing endoscopic images of the digestive organ using a neural network of a seventh embodiment is described. In the seventh embodiment, it is possible to use the region determination method for a digestive organ employing endoscopic images of the digestive organ using the neural network described in the first to the fourth embodiments. At S11, the neural network is trained using the first endoscopic images of the digestive organ and definitive information among information corresponding to the imaged region corresponding to the first endoscopic images. At S12, the trained neural network outputs, based on the second endoscopic images of the digestive organ, information corresponding to the imaged region of the digestive organ.

Eighth Embodiment

Figure 26:
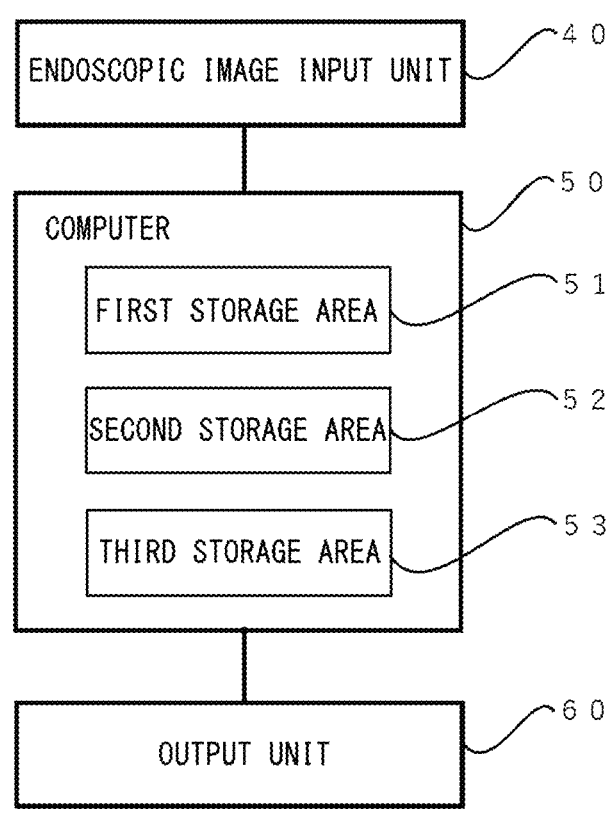
FIG. 26 is a diagram illustrating a region determination system for a digestive organ employing endoscopic images of the digestive organ using a neural network according to an eighth embodiment, a region determination program for a digestive organ employing endoscopic images of the digestive organ, and a computer-readable recording medium.

With reference to FIG. 26, a region determination system for a digestive organ employing endoscopic images of the digestive organ using a neural network of an eighth embodiment, a region determination program for a digestive organ employing endoscopic images of the digestive organ, and a computer-readable recording medium are described. In the eighth embodiment, it is possible to use the region determination system for a digestive organ employing endoscopic images of the digestive organ using the neural network described in the first to the fourth embodiments. The region determination system for a digestive organ employing endoscopic images of the digestive organ of the eighth embodiment includes an endoscopic image input unit 40, an output unit 60, and a computer 50 having the neural network embedded therein. The computer 50 includes a first storage area 51 that stores therein first endoscopic images of the digestive organ, a second storage area 52 that stores therein definitive information among information corresponding to an imaged region of the digestive organ, corresponding to the first endoscopic images, and a third storage area 53 that stores therein the neural network program. The neural network program stored in the third storage area 53 is trained based on the first endoscopic images stored in the first storage area 51 and definitive information stored in the second storage area 52. The neural network program outputs, based on the second endoscopic images of the digestive organ input from the endoscopic image input unit 40, information corresponding to the imaged region of the digestive organ corresponding to the second endoscopic images, to the output unit 60.

The region determination system for a digestive organ employing endoscopic images of the digestive organ includes the region determination program for a digestive organ employing endoscopic images of the digestive organ, the program causing a computer to operate as means. The region determination program for a digestive organ employing endoscopic images of the digestive organ can be stored in a computer-readable recording medium.

The invention claimed is:

1. A disease diagnosis support method employing endoscopic images of a digestive organ using a neural network, the method comprising training a neural network by using first endoscopic images of the digestive organ, and
corresponding to the first endoscopic images, at least one definitive diagnosis result of being positive or negative for a disease of the digestive organ, a past disease, a severity level, and information corresponding to an imaged region,
the trained neural network outputting, based on second endoscopic images of the digestive organ, at least one of a probability of being positive and/or negative for the disease of the digestive organ, a probability of the past disease, a severity level of the disease, and the information corresponding to the imaged region, wherein the first endoscopic images include at least one of:
(i) gastroscopic images, and the disease includes at least one of with or without *H. pylori* infection or with or without *H. pylori* eradication,
(ii) colon fiberscope images, the disease includes at least colitis ulcerosa, and the trained neural network outputs a result after being segmented in a plurality of stages according to the severity level of the colitis ulcerosa, or
(iii) esophagus endoscopic images with Endocytoscopy, the disease includes at least one of esophageal cancer, gastro-esophagus reflux disease, or esophagitis, and the trained neural network outputs a result after being segmented, for at least one of the esophageal cancer, the gastro-esophagus reflux disease, or the esophagitis.

2. The disease diagnosis support method employing endoscopic images of a digestive organ using a neural network according to claim 1, wherein the first endoscopic images are adjusted in contrast.

3. The disease diagnosis support method employing endoscopic images of a digestive organ using a neural network according to claim 1, wherein the first endoscopic images are associated with respective imaged regions.

4. The disease diagnosis support method employing endoscopic images of a digestive organ using a neural network according to claim 3, wherein the region includes at least one of a pharynx, an esophagus, a stomach, or a duodenum.

5. The disease diagnosis support method employing endoscopic images of a digestive organ using a neural network according to claim 3, wherein the region is segmented in a plurality of portions for at least one of the digestive organs.

6. The disease diagnosis support method employing endoscopic images of a digestive organ using a neural network according to claim 5, wherein when the region is a stomach, the segments include at least one of an upper stomach, a middle stomach, or a lower stomach.

7. The disease diagnosis support method employing endoscopic images of a digestive organ using a neural network according to claim 5, wherein when the region is a stomach, the segments include at least one of a cardia, a gastric fundus, a gastric corpus, an angular region, an antral zone, an antrum, or a pylorus.

8. The disease diagnosis support method employing endoscopic images of a digestive organ using a neural network according to claim 3, wherein when the number of the first endoscopic images in one of the imaged regions is smaller than that in another region, by using at least one of rotation, enlargement, reduction, change in the number of pixels, extraction of bright and dark portions, and extraction of portions having change in hue, for the first endoscopic images, the number of the first endoscopic images is made substantially equal in every region.

9. The disease diagnosis support method employing endoscopic images of a digestive organ using a neural network according to claim 3, wherein the trained neural network is capable of outputting information corresponding to a region at which the second endoscopic images have been imaged.

10. The disease diagnosis support method employing endoscopic images of a digestive organ using a neural network according to claim 9, wherein the trained neural network outputs the probabilities and the severity level together with information corresponding to the region.

11. The disease diagnosis support method employing endoscopic images of a digestive organ using a neural network according to claim 1, wherein the first endoscopic images include gastroscopic images, and the disease includes at least one of with or without *H. pylori* infection or with or without *H. pylori* eradication.

12. The disease diagnosis support method employing endoscopic images of a digestive organ using a neural network according to claim 1, wherein the first endoscopic images include colon fiberscope images, the disease includes at least colitis ulcerosa, and the trained neural network outputs a result after being segmented in a plurality of stages according to the severity level of the colitis ulcerosa.

13. The disease diagnosis support method employing endoscopic images of a digestive organ using a neural network according to claim 1, wherein the first endoscopic images include esophagus endoscopic images with Endocytoscopy, the disease includes at least one of esophageal cancer, gastro-esophagus reflux disease, or esophagitis, and the trained neural network outputs a result after being segmented, for at least one of the esophageal cancer, the gastro-esophagus reflux disease, or the esophagitis.

14. The disease diagnosis support method employing endoscopic images of a digestive organ using a neural network according to claim 1, wherein the second endoscopic images are at least one of images that are being captured with an endoscope, images transmitted via a communication network, images to be provided from a remote operation system or a cloud system, images stored in a computer-readable recording medium, or moving images.

15. The disease diagnosis support method employing endoscopic images of a digestive organ using a neural network according to claim 1, wherein a convolutional neural network is used as the neural network.

16. A disease diagnosis support system employing endoscopic images of a digestive organ, the system comprising an endoscopic image input unit, an output unit, and a computer having a neural network embedded therein, wherein the computer includes
a first storage area having first endoscopic images of a digestive organ stored therein,
a second storage area having, corresponding to the first endoscopic images, at least one definitive diagnosis result stored therein, the result being of being positive or negative for the disease of the digestive organ, a past disease, a severity level, and information corresponding to an imaged region, and
a third storage area having the neural network program stored therein,
the neural network program is trained based on the first endoscopic images stored in the first storage area and the definitive diagnosis result stored in the second storage area, and
the neural network program outputs, based on second endoscopic images of the digestive organ input from the endoscopic image input unit, at least one of a probability of being positive and/or negative for the disease of the digestive organ with respect to the second endoscopic images, a probability of a past disease, a severity level of the disease, and information corresponding to the imaged region, wherein the first endoscopic images include at least one of:
(i) gastroscopic images, and the disease includes at least one of with or without *H. pylori* infection or with or without *H. pylori* eradication,
(ii) colon fiberscope images, the disease includes at least colitis ulcerosa, and the trained neural network outputs a result after being segmented in a plurality of stages according to the severity level of the colitis ulcerosa, or (iii) esophagus endoscopic images with Endocytoscopy, the disease includes at least one of esophageal cancer, gastro-esophagus reflux disease, or esophagitis, and the trained neural network outputs a result after being segmented, for at least one of the esophageal cancer, the gastro-esophagus reflux disease, or the esophagitis.

17. The disease diagnosis support system employing endoscopic images of a digestive organ according to claim 16, wherein the first endoscopic images are adjusted in contrast.

18. The disease diagnosis support system employing endoscopic images of a digestive organ according to claim 16, wherein the first endoscopic images are associated with respective imaged regions.

19. The disease diagnosis support system employing endoscopic images of a digestive organ according to claim 18, wherein the region includes at least one of a pharynx, an esophagus, a stomach, or a duodenum.

20. The disease diagnosis support system employing endoscopic images of a digestive organ according to claim 18, wherein the region is segmented in a plurality of portions for at least one of the digestive organs.

21. The disease diagnosis support system employing endoscopic images of a digestive organ according to claim 20, wherein when the region is a stomach, the segments include at least one of an upper stomach, a middle stomach, or a lower stomach.

22. The disease diagnosis support system employing endoscopic images of a digestive organ according to claim 20, wherein when the region is a stomach, the segments include at least one of a cardia, a gastric fundus, a gastric corpus, an angular region, an antral zone, an antrum, or a pylorus.

23. The disease diagnosis support system employing endoscopic images of a digestive organ according to claim 16, wherein when the number of the first endoscopic images in one of the imaged regions is smaller than that in another region, by using at least one of rotation, enlargement, reduction, change in the number of pixels, extraction of bright and dark portions, and extraction of portions having change in hue, for the first endoscopic images, the number of pieces of training/validation data is made substantially equal in every region.

24. The disease diagnosis support system employing endoscopic images of a digestive organ according to claim 16, wherein the trained neural network program is capable of outputting information corresponding to a region at which the second endoscopic images have been imaged.

25. The disease diagnosis support system employing endoscopic images of a digestive organ according to claim 24, wherein the trained neural network program outputs the probabilities or the severity level together with the information corresponding to the region.

26. The disease diagnosis support system employing endoscopic images of a digestive organ according to claim 16, wherein the first endoscopic images include gastroscopic images, and the disease includes at least one of with or without *H. pylori* infection or with or without *H. pylori* eradication.

27. The disease diagnosis support system employing endoscopic images of a digestive organ using a neural network according to claim 16, wherein the first endoscopic images include colon fiberscopic images, the disease includes at least colitis ulcerosa, and the trained neural network program outputs a result after being segmented in a plurality of stages according to the severity level of the colitis ulcerosa.

28. The disease diagnosis support system employing endoscopic images of a digestive organ using a neural network according to claim 16, wherein the first endoscopic images include esophagus endoscopic images with Endocytoscopy, the disease includes at least one of esophageal cancer, gastro-esophagus reflux disease, or esophagitis, and the trained neural network outputs a result after being segmented, for at least one of the esophageal cancer, the gastro-esophagus reflux disease, or the esophagitis.

29. The disease diagnosis support system employing endoscopic images of a digestive organ using a neural network according to claim 16, wherein the second endoscopic images are at least one of images that are being captured with an endoscope, images transmitted via a communication network, images to be provided from a remote operation system or a cloud system, images stored in a computer-readable recording medium, or moving images.

30. The disease diagnosis support system employing endoscopic images of a digestive organ using a neural network according to claim 16, wherein the neural network is a convolutional neural network.

31. A non-transitory computer readable medium for storing a diagnosis support program based on endoscopic images of a digestive organ, the program causing a computer to operate as means in the disease diagnosis support system employing endoscopic images of a digestive organ according to claim 16.

32. A non-transitory computer-readable recording medium having the diagnosis support program stored therein based on endoscopic images of a digestive organ according to claim 31.

* * * * *